US012714661B2

(12) United States Patent
Willson

(10) Patent No.: US 12,714,661 B2
(45) Date of Patent: Aug. 25, 2026

(54) ORAL CARE COMPOSITIONS WITH PHOSPHOPEPTIDES FOR USE AGAINST DENTAL HYPERSENSITIVITY AND/OR XEROSTOMIA

(71) Applicant: DENTHERAPY LTD, Aberdeen (GB)

(72) Inventor: Richard Willson, Plymouth (GB)

( * ) Notice: Subject to any disclaimer, the term of this patent is extended or adjusted under 35 U.S.C. 154(b) by 300 days.

(21) Appl. No.: 18/579,107

(22) PCT Filed: Jul. 11, 2022

(86) PCT No.: PCT/GB2022/051790
§ 371 (c)(1), (2) Date: Jan. 12, 2024

(87) PCT Pub. No.: WO2023/285797
PCT Pub. Date: Jan. 19, 2023

(65) Prior Publication Data

US 2024/0325275 A1 Oct. 3, 2024

(30) Foreign Application Priority Data

Jul. 14, 2021 (GB) .................................... 2110114

(51) Int. Cl.
*A61K 8/64* (2006.01)
*A61K 8/19* (2006.01)
*A61Q 11/00* (2006.01)

(52) U.S. Cl.
CPC ................. *A61K 8/64* (2013.01); *A61K 8/19* (2013.01); *A61Q 11/00* (2013.01)

(58) Field of Classification Search
CPC ....................................................... A61K 8/64
See application file for complete search history.

(56) References Cited

FOREIGN PATENT DOCUMENTS

WO 20018087532 5/2018
WO 2020181335 9/2020

OTHER PUBLICATIONS

Alexandra Sbaraini et al., Experiences of oral health: before, during and after becoming a regular user of GC Tooth Mousse Plus, Research Square, Jan. 7, 2021, pp. 1-22, University of Melbourne.
International Search Report, PCT/GB2022/051790, Jul. 11, 2022, Dentherapy Ltd.
Written Opinion of the International Searching Authority, PCT/GB2022/051790, Nov. 7, 2022.
Siddhartha Chandel, et al., "The effect of sodium bicarbonate oral rinse on salivary pH and oral microflora: A prospective cohort study," National Journal of Maxillofacial Surgery, Jul.-Dec. 2017; 8(2): 106-109 (11 pages).

*Primary Examiner* — Benjamin J Packard
(74) *Attorney, Agent, or Firm* — Dickinson Wright PLLC

(57) ABSTRACT

The present invention relates to compositions for use in oral care and various methods of their use. In particular, it relates to compositions comprising phosphoproteins and their use in the treatment and prevention of dentine hypersensitivity and the treatment and prevention of xerostomia. Preferred compositions comprise osteopontin and derivatives thereof.

21 Claims, 4 Drawing Sheets

ORAL CARE COMPOSITIONS WITH PHOSPHOPEPTIDES FOR USE AGAINST DENTAL HYPERSENSITIVITY AND/OR XEROSTOMIA

CROSS-REFERENCE TO RELATED APPLICATIONS

The present application is a 35 U.S.C. Section 371 national stage filing of International Patent Application No. PCT/GB2022/051790, filed 11 Jul. 2022, and through which priority is claimed to UK application GB 2110114.2, filed 14 Jul. 2021.

The present invention relates to compositions for use in oral care and various methods of their use. In particular compositions comprising phosphoproteins and their use in the treatment and prevention of dentine hypersensitivity and the treatment and prevention of xerostomia.

BACKGROUND OF THE INVENTION

The following discussion is provided to aid the reader in understanding the disclosure and does not constitute any admission as to the contents or relevance of the prior art.

The dentine of a healthy tooth is protected by enamel and root cementum, but various factors such as gum recession and tooth wear can expose the dentine and lead to sensitivity. Dental hypersensitivity is characterised by a short sharp pain following a stimulus to the dental tissues. Exposure of dentine to a stimulus such as cold air and fluids results in disturbance of fluid flow in the dentinal tubules and distortion of the dental nerve fibres causing pain. Dental hypersensitivity only persists while the stimulus is applied or shortly after removal of the stimulus.

Open tubules are a significant factor in hypersensitivity. Sufferers of dentine hypersensitivity have considerably more open tubules on the dentine surface. To effectively treat hypersensitivity, occluding treatments must reduce or completely occlude the openings of tubules.

The majority of available treatments for hypersensitivity form a plug within the dentine surface layer and do not penetrate deep within the dentinal tubules. The surface plug is therefore prone to removal from acids and surface abrasion in the mouth. There is a need for providing a treatment that penetrates into the dentinal tubules and is resistant to removal by abrasion and an acidic environment.

Xerostomia, also known as dry mouth, is a condition caused by many different factors such as radiation during cancer treatment, prescription drugs, autoimmune conditions and other diseases affecting the salivary glands. Patients suffer from reduced saliva production which affects taste, chewing and swallowing. However, sufferers are also at higher risk of developing dental caries and developing infections such as candidiasis.

Saliva plays an important role in maintaining the oral pH and helps to buffer acid produced by bacteria that leads to dental caries. Reduced saliva production results in an imbalance in the oral environment and increased risk of demineralisation and developing dental caries.

Dental caries is a general healthcare challenge against which saliva plays a leading role in prevention and repair. However, in xerostomia patients, saliva in the mouth is reduced. The biggest chemical change resulting from reduced saliva is the dramatic decrease in the concentration of bicarbonate buffer. This concurrently reduces the buffering capacity of saliva and so the capacity of saliva to neutralise acidic attack. In addition, there is evidence to show that bicarbonate buffer in saliva inhibits the growth of biofilms. The formation of biofilms on oral surfaces increases colonies of acid producing bacteria as well as associated conditions such as calculus build-up. A reduction in bicarbonate buffer from saliva further removes the protection from the formation of biofilms therefore increasing the threat from the acid erosion and caries formation.

When there is less saliva in the mouth, such as in those patients that lack saliva due to xerostomia, buffering capacity is reduced, which leaves the enamel open to the effects of acid where calcium, phosphate and hydroxyl groups become ionised and solvated by the surrounding solvent. This process is then advanced further by acidic conditions in the mouth. The process is an equilibrium between the calcium, phosphate and hydroxide molecules in a solid crystal lattice and the corresponding ions in solution. The position of the equilibrium is dictated by: the pKa of the dissolving apatite, the pH of the solution and by the concentration of the ions in solution. In a healthy individual, during the day, saliva buffers the reaction and keeps this equilibrium balanced. However, this buffering capacity can drop in patients having xerostomia, and in such situations, there is a positive correlation between saliva buffering capacity and the prevalence of caries.

Existing treatments for xerostomia aim to alleviate discomfort of sufferers by providing artificial saliva and chewing sugar free gum. Topical fluoride applications and fluoride containing dentifrices are also used to manage the high risk of dental caries. However, there is a need for providing a treatment that addresses the dental caries and other infections that result from xerostomia, in combination with alleviating the discomfort of sufferers.

Therefore, there is a need for additional compositions to address the issues of (i) dentine hypersensitivity and (ii) xerostomia.

SUMMARY OF THE INVENTION

In a first aspect there is provided a composition comprising a phosphopeptide for use in preventing or treating dental hypersensitivity. In some embodiments, dental hypersensitivity is dentine hypersensitivity.

In a second aspect there is provided a composition comprising a phosphopeptide for use in preventing or treating xerostomia.

In some embodiments xerostomia is associated with Sjögren's Syndrome, cancer treatment, polypharma, and/or diseases of the salivary glands. In some embodiments the composition is for use in preventing or treating xerostomia induced demineralisation of an oral surface, dental caries and/or candidiasis infection. In some embodiments, the composition is for use in preventing or treating xerostomia by increasing the buffering capacity of saliva. In some embodiments the composition is for use in preventing or treating xerostomia induced demineralisation of an oral surface, dental caries and/or candidiasis infection by increasing the buffering capacity of saliva.

In a third aspect there is provided a composition comprising a phosphopeptide for use in preventing or treating demineralisation of an oral surface, enamel erosion, dental caries and/or candidiasis infection in patients having xerostomia.

In some embodiments, the composition is for use in preventing or treating demineralisation of an oral surface, enamel erosion, dental caries and/or candidiasis infection in patients having xerostomia by increasing the buffering capacity of saliva.

In one embodiment, there is provided a composition for use according to the first, second or third aspects, wherein the composition is for administration to the mouth of a subject and/or to an oral surface.

In some embodiments, the composition may be administered prior to sleep. In some embodiments, the composition may be administered in the evening or at night time. In one embodiment, the composition may be administered prior to sleep to increase the evening or night time buffering capacity of saliva. In one embodiment, the composition may be administered prior to sleep to provide an evening or night time buffering reservoir. In some embodiments, the evening or night time buffering reservoir is increased in patients having xerostomia. In one embodiment, the composition may be administered prior to sleep to prevent or treat xerostomia. In one embodiment, the composition may be administered prior to sleep to prevent or treat xerostomia induced demineralisation or dental caries. In one embodiment, the composition may be administered prior to sleep to prevent or treat xerostomia induced demineralisation or dental caries by increasing the evening or night time buffering capacity of saliva. Suitably the demineralisation or dental caries may be caused by xerostomia, or may be in a patient having xerostomia.

In some embodiments the composition may be administered after eating or drinking. In some embodiments the composition may be administered immediately after eating or drinking. In another embodiment, the composition may be administered within 2 hours after eating or drinking. Suitably, in some embodiments the composition is administered within 1 hour, within 30 minutes, within 15 minutes, within 10 minutes, within 5 minutes, within 2 minutes, within 1 minute after eating or drinking. In some embodiments the composition may be administered after eating or drinking to prevent or treat dental hypersensitivity. In some embodiments the composition may be administered after eating or drinking to prevent or treat xerostomia. In some embodiments the composition may be administered after eating or drinking to prevent or treat demineralisation of an oral surface, or dental caries induced by xerostomia.

In a fourth aspect, there is provided a method of treatment or prevention of dental hypersensitivity in a subject in need thereof, wherein the method comprises administering to the subject a therapeutically effective amount of a composition comprising a phosphopeptide.

In a fifth aspect there is provided a method of treatment or prevention of xerostomia in a subject in need thereof, wherein the method comprises administering to the subject a therapeutically effective amount of a composition comprising a phosphopeptide.

In a sixth aspect there is provided a method of treatment or prevention of demineralisation of an oral surface, dental caries and/or candidiasis infection in subject having xerostomia, wherein the method comprises administering to the subject a therapeutically effective amount of a composition comprising a phosphopeptide.

In a seventh aspect there is provided a method of maintaining enamel mineral density in a subject having hypersensitivity and/or xerostomia, wherein the method comprises administering to the subject a therapeutically effective amount of a composition comprising a phosphopeptide.

In an eighth aspect, there is provided a composition for use in maintaining enamel mineral density in a subject having hypersensitivity and/or xerostomia.

In a further aspect there is provided packaging comprising a composition for use according to any of the first, second, third, fourth, fifth, sixth, seventh or eighth aspects.

In some embodiments the packaging comprises an actuator operable to deliver a metered dose of the composition for use according to any of the first, second, third, fourth, fourth, fifth, sixth, seventh or eighth aspects when actuated. In some embodiments the actuator comprises a spray nozzle.

Suitable compositions for any of the above aspects are discussed below.

In some embodiments of the above aspects, the composition comprises osteopontin or phosphopeptides derived therefrom, and/or casein or phosphopeptides derived therefrom.

Suitably the compositions of any of the above aspects may or may not comprise fluoride. In some embodiments of the above aspects, the composition further comprises fluoride or a source of fluoride, such as, but not limited to, monofluorophosphate. In some embodiments of the above aspects the composition does not comprise fluoride or a source of fluoride. Suitably, in some embodiments, where the composition does not comprise additional phosphate or an additional source of phosphate, the composition further does not comprise fluoride or a source of fluoride. Alternatively, in some embodiments where the composition does not comprise additional phosphate or an additional source of phosphate, the composition comprises fluoride or a source of fluoride.

Suitably the compositions of any of the above aspects may or may not comprise calcium. In some embodiments of the above aspects, the composition further comprises calcium or a source of calcium. In some embodiments, the composition does not comprise calcium or a source of calcium. Suitably, in an embodiment where the composition is for use in treatment or prevention of dental hypersensitivity, the composition comprises calcium or a source of calcium.

The present inventors have discovered compositions which solve the above-mentioned problems of (i) dental hypersensitivity, and/or (ii) xerostomia.

With regard to preventing or treating hypersensitivity, the present inventors have discovered that a composition comprising a phosphopeptide with a supersaturated concentration of calcium can penetrate deep within the dentinal tubules. Conventional treatments rely on plugging the tubules a few micrometers below the tubule surface, which is then prone to removal from acids and surface abrasion. The composition of the present invention results in effective plugging of the tubule depositing inorganic macromolecules deep within the dentine network. This has the advantage of not being eroded by acids or abrasion. Use of these compositions for preventing or treating hypersensitivity have not been described before.

With regard to treating or preventing xerostomia, the inventors have further discovered that a composition comprising a phosphopeptide, provides relief from the symptoms of xerostomia by an improved mouth feel, and also facilitates remineralisation and/or reduces demineralisation and facilitates prevention of dental caries as well as other oral infections typically associated with xerostomia. Without being bound by theory, the inventors believe that a composition of the present invention has the advantage of reducing acid erosion and caries formation when the buffering capacity of oral saliva is low such as in xerostomia. The compositions of the invention can be used to increase buffering capacity of saliva in those with the condition, in order to address the underlying cause of demineralisation and dental caries.

Use of these compositions for preventing or treating xerostomia have not been described before.

Further features and embodiments of the above aspects are defined hereinbelow under headed sections. Any feature in any section may be combined with any aspect or embodiment in any workable combination.

Compositions:

The compositions of the present invention are suitably oral care compositions, which may be for use in preventing or treating dental hypersensitivity, or xerostomia.

Suitably the compositions of the invention may be a fluid or a solid. Suitably the compositions of the invention may be a fluid. Suitably, a fluid may be a liquid. In some embodiments the liquid is a colloid. Suitably, the compositions may be an oral spray; a mouthwash; a toothpaste, a cream, a gel, a serum; chewing gum, powder or granules; wafer tabs; delivery strips; tablets; capsules; or the like.

Suitably any of the components described herein may be mixed in any workable combination to form a composition of the invention falling within one of the above aspects.

Suitably, the composition is an aqueous composition, suitably an aqueous fluid. Suitably, the composition may therefore comprise an aqueous medium. Suitably the composition may comprise about 20%, about 25%, about 30%, about 35%, about 40%, about 45%, about 50%, about 55%, about 60%, about 65%, about 70%, about 75%, about 80%, about 90% by weight of water. Suitably the composition may comprise between about 20% to about 75% by weight of water.

Suitably, in one embodiment, the composition may be liquid. Suitably an aqueous liquid. Suitably in such embodiments, the composition comprises at least 30%, suitably at least 40%, suitably at least 50% by weight of water. Suitably in such embodiments, the composition may be a mouth wash or an oral spray.

Suitably, in an alternative embodiment, the composition may be a colloid. Suitably a colloidal composition may encompass a gum, gel, tablet or paste, for example. Suitably in such embodiments, the composition comprises less than 25% by weight of water. Suitably in such embodiments, the composition may be a toothpaste. In one embodiment the composition is a gel. Suitably, in some embodiments the gel composition does not comprise a thickener such as xanthan gum and/or silica. In another embodiment, the gel composition comprises a thickener such as xanthan gum and/or silica.

Suitably, in some embodiments, the composition may comprise phosphate, fluoride and/or calcium, or a source thereof, unless otherwise stated. Suitable sources of these components are described elsewhere herein.

In some embodiments, the composition may comprise a phosphopeptide, a source of calcium ions and a source of phosphate ions, and optionally a source of fluoride.

In one embodiment, the composition may comprise a phosphopeptide, a source of calcium ions and does not further comprise additional phosphate or an additional source of phosphate. Suitably, in some embodiments, where the composition does not comprise additional phosphate or an additional source of phosphate, the composition further does not comprise fluoride or a source of fluoride. Alternatively, in some embodiments where the composition does not comprise additional phosphate or an additional source of phosphate, the composition comprises fluoride or a source of fluoride. Suitably, in some embodiments, the phosphopeptide is osteopontin or phosphopeptides derived therefrom, and/or casein or phosphopeptides derived therefrom. Suitable sources calcium, phosphate and fluoride are described elsewhere herein. Suitably, in some embodiments, the composition may comprise a stabilised amorphous calcium phosphate. In another embodiment the composition may comprise a stabilised amorphous calcium phosphate and fluoride. Suitably, the composition may comprise any composition as described in WO2018/087532. In another embodiment, the composition may comprise any composition as described in WO1998/040406 or WO2006/056013.

Suitably the composition may further comprise other components, suitably the other components are liquid or soluble. Suitably the other components may be selected from: one or more of alcohol(s), humectant(s), surfactant(s), preservative(s), flavouring agent(s), sweetening agent(s), colouring agent(s), anti-caries agent(s), buffer(s), acid(s), base(s), whitening agent(s), thickener(s), and anticalculus agent(s).

The amounts of the various components of the compositions of the present invention can of course be determined by the person skilled in the art. Suitably the amounts of the various components making up a composition add up to 100% w/w of the composition.

Suitably, the composition may comprise a pH buffering agent (or buffer). Various pH buffering agents are well-known to the skilled person. Exemplary buffers include, but are not limited to, phosphate buffers, Tris (tris(hydroxymethyl)aminomethane) buffers, and sodium bicarbonate. In one embodiment, the buffer is sodium bicarbonate.

Suitably, the pH buffering agent maintains the composition at a pH of above 7, suitably in the range of from pH 7 to 9, suitably in the range of pH 7.1 to 8.5, suitably in the range of pH 7.2 to 8. Suitably said pH is maintained for a period of storage at room temperature of at least 6 weeks, 3 months, 6 months, suitably at least 1 year. Suitable buffering agents to achieve this will be apparent to the skilled person and their suitability for purpose can be readily determined experimentally. In one embodiment, the pH of the composition is stable for at least 10 months.

Suitably the initial pH of the composition may be adjusted by the addition of hydrogen ions (acid) or hydroxide ions (base), as required. Any physiologically compatible or acceptable acid or base may typically be used, e.g. hydrochloric acid (HCl) and sodium hydroxide (NaOH). Suitably once the desirable pH is reached, the buffer acts to maintain the pH.

Suitably the composition may or may not comprise one or more alcohols. Exemplary alcohols include, but are not limited to, ethanol, or isopropanol. Suitably, the compositions of the invention may comprise a sweetener alcohol, as explained below, however suitably no other additional alcohol is present. In one embodiment, therefore, the compositions of the invention do not contain ethanol or isopropanol.

Suitably, where additional alcohol is present, the weight ratio of water to alcohol is in the range of from about 1:1 to about 20:1. Suitably, the total amount of water-alcohol mixture in this type of preparation is typically in the range of from about 70 to about 99.9% by weight of the preparation. Suitably the concentration of the additional alcohol may be between 1-99%.

Suitably the composition may comprise one or more sweeteners. Suitably the sweeteners may also be alcohols. Alternatively, the sweeteners may be natural or synthetic sugars such as saccharine. Suitably the composition may comprise both saccharine and an alcohol sweetener. Exemplary alcohol sweeteners include, but are not limited to, xylitol or mannitol. In one embodiment the sweetener is xylitol, suitably when the composition is a liquid such as a mouthwash or oral spray. In one embodiment, the sweetener is mannitol, suitably when the composition is a colloid, such as toothpaste or gel.

Suitably the composition may comprise a whitening agent. Suitably the whitening agent may be chemical or abrasive. Exemplary chemical whitening agents include, but are not limited to; sodium bicarbonate or hydrogen peroxide. Exemplary abrasive whitening agents include, but are not limited to; microparticles such as silica, or charcoal. In one embodiment, the whitening agent is Zeofree 113 microparticles, suitably when the composition is a colloid such as toothpaste.

Suitably the composition may comprise a thickener. Examples of thickeners include, but are not limited to, silica or xanthan gum. In one embodiment, the thickening agent comprises Zeofree 153 microparticles and xanthan gum, suitably when the composition is a colloid such as toothpaste.

Suitably the composition may comprise a flavouring agent. Suitably the flavouring agent comprises a number of different chemicals which may be natural or synthetic such as sugars, oils, esters, and the like. In one embodiment, the flavouring agent may comprise a mixture of saccharine, tego betain, and flavour oil. An exemplary flavouring agent may comprise the following (values provided as per amounts in the final composition):

- Sodium methyl paraben; suitably in an amount of about 0.02% w/w
- Phenoxyethanol; suitably in an amount of about 0.2% w/w
- Saccharine; suitably in an amount of about 0.08% w/w
- Tego betain; suitably in an amount of about 0.6% w/w
- Water; suitably in an amount of about 6.3% w/w, suitably wherein the water is deionised water
- Flavour oil; suitably in an amount of about 0.5% w/w Suitably the flavour oil may comprise a natural or synthetic flavouring. Suitably the flavour oil may comprise a herb or plant extract. Suitably the flavour oil may comprise a mint flavour.

Suitably the composition may comprise a preservative. Examples of preservative include sodium methyl paraben and phenoxyethanol. Suitably the preservative may comprise sodium methyl paraben; suitably in an amount of about 0.02% w/w and phenoxyethanol; suitably in an amount of about 0.2% w/w.

Suitably, the composition may comprise any of the following components: water, buffer(s), a source of calcium ions, a source of phosphate ions, a phosphopeptide, a source of fluoride ions, a flavouring, a preservative, a sweetener, an acid, a whitening agent, a thickener.

Suitably, the composition comprises at least the following components: water, buffer(s), a source of calcium ions, a phosphopeptide. In one embodiment, the composition comprises the following components: water, buffer(s), a source of calcium ions, a phosphopeptide, a source of fluoride ions, a flavouring and preservative, a sweetener, an acid. In one embodiment, the composition comprises the following components: water, buffer(s), a source of calcium ions, a phosphopeptide, a source of fluoride ions, a flavouring and preservative, a sweetener, an acid, a whitening agent, a thickener.

In some embodiments of the present invention, the components of the composition may individually be provided in the following amounts, or in any combination:

- Water—from about 20% to about 99% by weight; suitably from about 23% to about 66% by weight;
- A buffer—from about 1% to about 20% by weight; suitably from about 1% to about 15% by weight;
- A source of calcium ions if present (e.g. a soluble calcium salt or other options as discussed herein)—from about 0.1% to about 15% by weight; suitably from about 0.1% to about 5% by weight;
- A source of phosphate ions if present (e.g. a soluble phosphate salt or other options as discussed herein)—from about 0.2% to about 32% by weight, from about 0.2% to about 15% by weight; suitably from about 0.5% to about 5% w/v, suitably from about 0.7% to about 2% by weight, e.g. from 0.8 to 1.2% by weight.
- A phosphopeptide—from about 0.5% to about 15% w/v; suitably from about 1% to about 10% by weight, suitably from about 1.5% to about 5% by weight, e.g. from 2 to 4% by weight.
- A source of fluoride ions if present (e.g. a soluble fluoride salt such as monofluorophosphate as discussed herein)—from about 0.01% to about 3%; suitably from about 0.05% to about 1.5% by weight.

In some embodiments, the compositions may further comprise any of the following components alone, or in any combination:

- A flavouring, preservative and/or other ingredients from about 0% to about 70% by weight; suitably from about 0% to about 20% by weight; suitably from about 0% to about 10% by weight;
- A sweetener (e.g. a sweetener alcohol such as mannitol or xylitol)—from about 0.1% to about 20% (w/w); suitably from about 0.1% to about 10% (w/w);
- An acid (e.g. HCl)—from about 5-40% (w/w); suitably from about 10-35% (w/w);
- A whitening agent (e.g. abrasive silica)—from about 1-20% (w/w); suitably from about 5-10% (w/w);
- A thickener (e.g. xanthan gum and/or silica)—from about 0.1-20% (w/w), suitably from about 0.5-15% (w/w)

As noted above, in one embodiment, the composition is an oral spray or mouthwash. Exemplary mouthwash and spray formulations are set out below.

Mouth washes and mouth sprays according to the present invention can suitably include the following exemplary components by weight:

- water (suitably from about 45% to about 95%),
- ethanol (suitably from about 0% to about 25%),
- humectant(s) (suitably from about 0% to about 50%),
- surfactant(s) (suitably from about 0.01% to about 7%),
- flavouring agent(s) (suitably from about 0.04% to about 2%),
- sweetening agent(s) (suitably from about 0.1% to about 8%),
- colouring agent(s) (suitably from about 0% to about 0.5%),
- xylitol (suitably from about 0% to about 8%),
- anti-caries agent(s), including but not limited to stabilised calcium phosphate and fluoride (suitably from about 0.001% to 10%), and optionally
- an anti-calculus agent (suitably from about 0% to about 13%).

One exemplary composition of the present invention comprises:

- a phosphopeptide; suitably in an amount of about 3% w/w, suitably wherein the phosphopeptide comprises osteopontin (OPN) or phosphopeptides derived from OPN, for example wherein the phosphopeptide is OPN-10;
- a buffer; suitably in an amount of about 15% w/w, suitably of a 1M solution, suitably wherein the buffer is sodium bicarbonate;
- water; suitably in an amount of about 54% to 66% w/w, suitably wherein the water is deionised water;

a source of calcium; suitably in an amount of about 3% w/w, suitably 2.9% w/w, suitably wherein the source of calcium is a calcium chloride solution, suitably wherein the calcium chloride solution is about 1M;

optionally, a source of fluoride suitably in an amount of about 0.4% to 0.5% w/w, suitably 0.4% w/w, suitably wherein the source of fluoride is monofluorophosphate;

a sweetener; suitably in an amount of about 5% w/w, suitably wherein the sweetener is xylitol;

optionally an acid; suitably in an amount of about 11% w/w, suitably wherein the acid is hydrochloric acid, suitably wherein the hydrochloric acid is about 1M; and a flavouring and preservative agent; suitably in an amount of about 8% w/w, suitably 7.7% w/w, suitably wherein the agent comprises a mixture of sodium methyl paraben, phenoxyethanol, saccharine, tego betain, and flavour oil.

Suitably such an exemplary composition is a liquid. Suitably such an exemplary composition is a mouth wash or an oral spray. Suitably such an exemplary composition may be known as 'MOL'.

A further exemplary composition of the present invention comprises:

a phosphopeptide; suitably in an amount of about 3% w/w, suitably wherein the phosphopeptide comprises OPN or phosphopeptides derived from OPN, for example wherein the phosphopeptide is OPN-10;

a buffer; suitably in an amount of about 15% w/w, suitably of a 1M solution, suitably wherein the buffer is sodium bicarbonate;

water; suitably in an amount of about 30% w/w, suitably wherein the water is deionised water;

a source of calcium; suitably in an amount of about 3% w/w, suitably 2.9% w/w, suitably wherein the source of calcium is a calcium chloride solution, suitably wherein the calcium chloride solution is about 1M;

a source of phosphate; suitably wherein the source of phosphate is trisodium phosphate solution in an amount of about 16% w/w and disodium hydrogen phosphate solution in an amount of about 16% w/w, suitably wherein the trisodium phosphate solution is about 0.1M and wherein the disodium hydrogen phosphate solution is about 0.1M;

optionally, a source of fluoride suitably in an amount of about 0.4% to 0.5% w/w, suitably 0.4% w/w, suitably wherein the source of fluoride is monofluorophosphate;

a sweetener; suitably in an amount of about 5% w/w, suitably wherein the sweetener is xylitol; and a flavouring and preservative agent; suitably in an amount of about 8% w/w, suitably 7.7% w/w, suitably wherein the agent comprises a mixture of sodium methyl paraben, phenoxyethanol, saccharine, tego betain, and flavour oil.

Suitably such an exemplary composition is a liquid. Suitably such an exemplary composition is a mouth wash or an oral spray or a gel. Suitably such an exemplary composition may be known as 'MOK'.

In some embodiments, the exemplary compositions above do not comprise a source of fluoride. Suitably they do not comprise monofluorophosphate.

In some embodiments, the exemplary composition above does not comprise an acid. Suitably it does not comprise hydrochloric acid.

Suitably, water is added to make up the final composition to 100% w/w. Suitably, in the absence of any component, further water is added instead. In one embodiment, the water is in an amount of 55% w/w. In one embodiment the water is in an amount of 55.4% w/w, suitably in such an embodiment, the composition does not comprise a source of fluoride. In one embodiment, the water is in an amount of 66.4% w/w, suitably in such an embodiment, the composition does not comprise a source of fluoride or an acid.

Suitably the MOL or MOK composition may be used in any aspect of the invention, for prevention or treatment of dental hypersensitivity, preferably dentine hypersensitivity, or for prevention and/or treatment of xerostomia, and/or preventing or treating demineralisation of an oral surface, dental caries and/or candidiasis infection in patients having xerostomia. Suitably, the MOL or MOK composition may be used in any method of treating or preventing dental hypersensitivity or methods of treating or preventing xerostomia and/or preventing or treating demineralisation of an oral surface, dental caries and/or candidiasis infection in patients having xerostomia. In another embodiment, the MOL or MOK composition may be used in a method of maintaining enamel mineral density in a subject having hypersensitivity and/or xerostomia. Suitably, in some embodiments the MOK composition is a gel.

Another exemplary composition of the present invention comprises:

a phosphopeptide; suitably in an amount of about 3% w/w; suitably wherein the phosphopeptide comprises OPN or phosphopeptides derived from OPN, for example wherein the phosphopeptide is OPN-10;

a buffer; suitably in an amount of about 2% w/w, suitably wherein the buffer is sodium bicarbonate;

a whitening agent; suitably in an amount of about 6% w/w, suitably wherein the whitening agent comprises an abrasive silica, for example zeofree 113;

water; suitably in an amount of about 23 to 25% w/w, suitably wherein the water is deionised water;

an acid; suitably in an amount of about 34% w/w, suitably wherein the acid is hydrochloric acid, suitably wherein the hydrochloric acid is about 1M;

a source of calcium; suitably in an amount of about 0.5% w/w, suitably wherein the source of calcium is calcium chloride;

optionally a source of fluoride, suitably in an amount of about 1% w/w, suitably 1.1% w/w, suitably wherein the source of fluoride is monofluorophosphate;

a sweetener; suitably in an amount of about 9% w/w, wherein suitably the sweetener is mannitol;

a thickener; suitably in an amount of about 13% w/w, suitably 12.8% w/w, wherein suitably the thickener comprises a thickening silica and xanthan gum, for example Zeofree 153 and xanthan gum; and a flavouring and preservative agent; suitably in an amount of about 8% w/w, suitably 7.7% w/w, suitably wherein the agent comprises a mixture of sodium methyl paraben, phenoxyethanol, saccharine, tego betain, and flavour oil.

Suitably such an exemplary composition is a colloid. Suitably such an exemplary composition is a toothpaste. Suitably such an exemplary composition may be known as 'MON'.

In some embodiments, the exemplary composition above does not comprise a source of fluoride. Suitably it does not comprise monofluorophosphate.

Suitably, water is added to make up the final composition to 100% w/w. Suitably, in the absence of any component, further water is added instead. In one embodiment, the water is in an amount of 23.9% w/w. In one embodiment, the water is in an amount of 25% w/w, suitably in such an embodiment, the composition does not comprise a source of fluoride.

Suitably the MON composition may be used for prevention or treatment of dental hypersensitivity, preferably dentine hypersensitivity, or for prevention and/or treatment of xerostomia, and/or preventing or treating demineralisation of an oral surface, dental caries and/or candidiasis infection in patients having xerostomia. Suitably, the MON composition may be used in any method of treating or preventing dental hypersensitivity or methods of treating or preventing xerostomia and/or preventing or treating demineralisation of an oral surface, dental caries and/or candidiasis infection in patients having xerostomia. In another embodiment, the MON composition may be used in a method of maintaining enamel mineral density in a subject having hypersensitivity and/or xerostomia.

Phosphopeptides:

The term “phosphopeptides” is used herein to describe phosphorylated polypeptides in a general sense. The term phosphopeptides is used interchangeably with phosphoprotein unless the context dictates otherwise. A range of phosphopeptides that can be used in the present invention are well-known in the art, and several are described in detail below.

Phosphopeptides that are able to interact with and stabilise calcium phosphate complexes are of particular interest, though it will be noted that in the present invention the phosphopeptides need not perform such a role, e.g. when additional phosphate or an additional source of phosphate is absent.

In particular, mention can be made of osteopontin or phosphopeptides derived therefrom, and casein or phosphopeptides derived therefrom. These two phosphoproteins and their phosphopeptides have been extensively discussed in the literature in respect of forming stabilised calcium phosphate complexes. However, there are other phosphopeptides which can form stabilised calcium phosphate complexes, such as phosvitin (Swiss-Prot Accession No P67869), fetuin A (FETUA) (Swiss-Prot Accession No P02765), proline-rich basic phosphoprotein 4 (PRB4) (Swiss-Prot Accession No PI 0163), matrix Gla protein (MGP) (Swiss-Prot Accession No P08493), secreted phosphoprotein 24 (SPP-24) (Swiss-Prot Accession No Q13103), Riboflavin Binding Protein (Swiss-Prot Accession No P02752), integrin binding sialophosphoprotein II (IBSP-II) (Swiss-Prot Accession No P21815), matrix extracellular bone phosphoglycoprotein (MEPE) (Swiss-Prot Accession No Q9NQ76), dentin matrix acidic phosphoprotein 1 (OMP1) (Swiss-Prot Accession No Q13316), human beta-casein, bovine beta-casein, and isoforms or phosphopeptides derived therefrom. Moreover, there are potentially a wide range of synthetic phosphopeptides that can be used in the present invention.

Thus, suitable phosphopeptides may be from any source and take a number of forms. For example, suitable phosphopeptides include full length phosphoproteins, or smaller phosphopeptides derived therefrom that may be naturally occurring or may be formed or isolated by tryptic or chemical (e.g. alkaline hydrolysis) digestion of such phosphoproteins, or obtained by chemical or recombinant synthesis. The phosphopeptide may be osteopontin or casein, or may be derived from osteopontin, casein, or other phosphoamino acid rich proteins such as phosvitin (Swiss-Prot Accession No P67869), fetuin A (FETUA) (Swiss-Prot Accession No P02765), proline-rich basic phosphoprotein 4 (PRB4) (Swiss-Prot Accession No PI 0163), matrix Gla protein (MGP) (Swiss-Prot Accession No P08493), secreted phosphoprotein 24 (SPP-24) (Swiss-Prot Accession No Q13103), Riboflavin Binding Protein (Swiss-Prot Accession No P02752), integrin binding sialophosphoprotein II (IBSP-II) (Swiss-Prot Accession No P21815), matrix extracellular bone phosphoglycoprotein (MEPE) (Swiss-Prot Accession No Q9NQ76), dentin matrix acidic phosphoprotein 1 (OMP1) (Swiss-Prot Accession No Q13316), human beta-casein, bovine beta-casein, and isoforms or phosphopeptides derived therefrom.

In one embodiment, phosphopeptides obtained by enzymatic (e.g. tryptic) digest of osteopontin or casein are used in the present invention.

Osteopontin (OPN) is a protein that can be obtained from milk. For example, bovine OPN can be isolated by anion exchange chromatography from e. g. acid whey at pH 4.5 as described by the patent applications WO 01/497741, WO 02/28413, WO 2012/117,119 or WO 2012/117,120. An OPN purity of up to 90-95% can be obtained. The present invention can use naturally occurring fragments or peptides derived from OPN by proteolytic cleavage in the milk, or genesplice-, phosphorylation-, or glycosylation variants as obtainable from the method proposed in, for example, WO 01/49741 and WO2013/144247. OPN can be derived from milk from any milk producing animals, such as cows, humans, camels, goats, sheep, dromedaries and llamas. OPN from bovine milk is typically preferred due to availability and characterisation in the literature. OPN is present in bovine milk, both in the form of full length bovine OPN (e.g. position 17-278 of Swiss-Prot Accession No P31096, or a peptide having at least 95% sequence identity with position 17-278 of Swiss-Prot Accession No P31096) and in the form of a long N-terminal fragment of full length bovine OPN (e.g. position 17-163 of Swiss-Prot Accession No P31096, or a peptide having at least 95% sequence identity with position 17-163 of Swiss-Prot Accession No P31096), see e.g. Bissonnette et al., Journal of Dairy Science Vol. 95 No. 2, 2012). Full length OPN is an acidic, highly phosphorylated, sialic acid rich, calcium binding protein. Full length osteopontin binds 28 moles of phosphate and about 50 moles of Ca per mole. The use of OPN to form calcium phosphate complexes is discussed extensively in, for example, WO2013/144247, particularly but not exclusively in respect of their use to treat biofilm related diseases.

In some embodiments of the invention, the OPN or phosphopeptides derived therefrom may be substantially pure full length bovine OPN, it may be a substantially pure, long N-terminal fragment of full length bovine OPN, and it may be a mixture comprising full length bovine OPN and the long N-terminal fragment of full length bovine OPN. Such a mixture may for example contain full length bovine OPN in an amount of 5-40% (w/w) relative to the total amount of OPN and the long n-terminal fragment of full length bovine OPN in an amount of 60-95% (w/w) relative to the total amount of OPN.

In one embodiment, the compositions of the invention comprise phosphopeptides derived from OPN (e.g. by the cleavage of OPN, such as by tryptic or chemical (e.g. alkaline hydrolysis) digestion of OPN). In one embodiment, the compositions of the invention comprise OPN-derived phosphopeptides sold commercially as Lacprodan® OPN-10. OPN-10 is available commercially from Arla Foods Ingredients (Arla Foods Ingredients Group P/S, Sonderhøj 10-12, 8260 Viby J, Denmark), and contains fractionated osteopontin from bovine milk.

Casein and casein-derived phosphopeptides are discussed at length in WO 98/40406 and WO 2006/135982, and these phosphopeptides can also suitably be used in the present invention.

As discussed in WO 2006/135982, CPP can form a colloidal complex with amorphous calcium phosphate, where the core particles aggregate to form large (e.g. 100 nm) colloidal particles suspended in water. It is believed that this general method of stabilisation of calcium phosphate also occurs for other phosphoproteins. Without wishing to be bound by theory, the phosphopeptide seems to bind to an amorphous calcium phosphate (ACP) cluster to produce a metastable solution in which growth of ACP to a size that initiates nucleation and precipitation is prevented.

Suitably, phosphopeptides comprising the motif Ser(P)-Ser(P)-Ser(P)-Glu-Glu, which is present in casein phosphopeptides may be used in the present invention. However, phosphopeptides comprising other sequence motifs rich in phosphoamino acids are also of use in the present invention.

Suitably, casein-derived phosphopeptides comprising the sequences $\alpha_{s1}$(59-79), $\beta$(1-25), $\alpha_{s2}$(46-70) and $\alpha_{s1}$(1-21), as set out in WO 98/40406 and WO 2006/135982, may be used in the present invention. Additional flanking sequences surrounding these core sequences may be present, in which case they can be wild type sequences or may optionally be modified by deletion, addition or conservative substitution of one or more residues.

Accordingly, in embodiments of the present invention, the phosphopeptide comprises osteopontin or phosphopeptides derived therefrom, or casein or phosphopeptides derived therefrom. In some embodiments, the calcium phosphate-stabilising agent comprises osteopontin-derived phosphopeptides or casein-derived phosphopeptides.

Alternatively or additionally, the phosphopeptide comprises one or more phosphoproteins selected from the group consisting of phosvitin (Swiss-Prot Accession No P67869), fetuin A (FETUA) (Swiss-Prot Accession No P02765), proline-rich basic phosphoprotein 4 (PRB4) (Swiss-Prot Accession No PI 0163), matrix Gla protein (MGP) (Swiss-Prot Accession No P08493), secreted phosphoprotein 24 (SPP-24) (Swiss-Prot Accession No Q13103), Riboflavin Binding Protein (Swiss-Prot Accession No P02752), integrin binding sialophosphoprotein II (IBSP-II) (Swiss-Prot Accession No P21815), matrix extracellular bone phosphoglycoprotein (MEPE) (Swiss-Prot Accession No Q9NQ76), dentin matrix acidic phosphoprotein 1 (OMP1) (Swiss-Prot Accession No Q13316), human beta-casein, bovine beta-casein, and isoforms or phosphopeptides derived therefrom.

For the avoidance of doubt, it should be noted that in embodiments of the present invention, the compositions can comprise a mixture of different phosphopeptides. For example, the composition may comprise a mixture of different phosphopeptides derived from a single phosphoprotein (e.g. casein or OPN). Alternatively, the calcium phosphate-stabilising agent may comprise a mixture of different phosphoproteins (e.g. a mixture of casein and OPN, or other different phosphoproteins) and/or phosphopeptides derived from a mixture of more than one different phosphoprotein (e.g. a mixture of phosphopeptides derived from both casein and OPN). In many cases, the composition will comprise a heterogeneous mixture of phosphopeptides obtained by the cleavage of a naturally occurring protein, such as OPN or casein.

Stabilised Calcium Phosphate Complexes:

A "stabilised calcium phosphate complex" is a complex comprising calcium, phosphates and a calcium phosphate-stabilising agent (usually a phosphopeptide). The stabilised calcium phosphate complex is typically soluble or at least metastable in the liquid medium in which it is contained, i.e. the liquid composition. Calcium phosphate-stabilising agents (such as phosphopeptides) are able to bind to calcium phosphate complexes and prevent them from precipitating. In particular, amorphous calcium phosphate complexes can be stabilised in a form in which they remain soluble (or metastable) and are able to release calcium and phosphate.

Without wishing to be bound by theory, small amounts of phosphopeptide stabilised calcium phosphate complexes may be formed upon administration to the mouth of a suitable liquid composition containing a phosphopeptide and a source of calcium ions. Stabilised calcium phosphate complexes may be formed on interaction of exogenous calcium ions with phosphate ions present in saliva of the mouth.

Nonetheless, it is remarkable how the compositions of some of the aspects of the invention that do not comprise additional phosphate or an additional source of phosphate can still achieve high levels of remineralisation.

A "calcium phosphate-stabilising agent" is an agent that is capable of binding to and stabilising calcium phosphate in a stabilised calcium phosphate complex. Suitably, the calcium phosphate may be stabilised as amorphous calcium phosphate. Suitable calcium phosphate-stabilising agents include phosphopeptides, as explained above. Suitable phosphopeptides are defined herein.

Suitably compositions of certain aspects of the present invention do not comprise a stabilised calcium phosphate complex. Suitably compositions of certain aspects of the present invention do not comprise amorphous calcium phosphate. Suitably in aspects or embodiments where the composition does not comprise additional phosphate or an additional source of phosphate, suitably the composition does not comprise a calcium phosphate complex such as amorphous calcium phosphate.

Suitably, these compositions may comprise a negligible amount of a stabilised calcium phosphate complex. By a negligible amount, it is meant that these compositions comprise less than 1% w/w of a stabilised calcium phosphate complex, suitably less than 0.9% w/w, suitably less than 0.8% w/w, suitably less than 0.7% w/w, suitably less than 0.6% w/w, suitably less than 0.5% w/w, suitably less than 0.4% w/w, suitably less than 0.3% w/w, suitably less than 0.2% w/w, suitably less than 0.1% w/w. In one embodiment, the compositions that do not comprise additional phosphate or an additional source of phosphate comprise less than 0.1% w/w of a stabilised calcium phosphate complex.

In some embodiments, compositions of certain aspects of the present invention comprise a stabilised calcium phosphate complex.

Calcium and Sources of Calcium:

The compositions of the invention may comprise calcium or a source of calcium.

In one embodiment, the compositions of the first aspect for use in treatment or prevention of dental hypersensitivity may comprise calcium or a source of calcium. In one embodiment, the compositions of the first aspect for use in treatment or prevention of dental hypersensitivity may comprise supersaturated calcium.

In one embodiment, the compositions of the second aspect for use in prevention or treatment of xerostomia may comprise calcium or a source of calcium.

In one embodiment, the compositions of the third aspect for use in prevention or treatment of demineralisation or caries associated with xerostomia may comprise calcium or a source of calcium.

Suitably, in one embodiment, the compositions for use in the methods of the fourth, fifth, sixth, seventh or eighth aspects as described herein may comprise calcium or a source of calcium. It may be preferable in some embodiments that the composition comprises supersaturated calcium.

Calcium and sources of calcium as used herein refers to any suitable source of calcium ions. A source of calcium ions should be able to dissolve in the liquid medium to release calcium ions. Suitably the source of calcium ions may be a soluble calcium salt. Suitably the source of calcium ions has a solubility of 5 g per 100 ml of liquid medium or higher, 10 g per 100 ml of liquid medium or higher, or 50 g per 100 ml of liquid medium or higher. The source of calcium ions can be provided in solid form or be dissolved in a suitable liquid.

One particularly suitable source of calcium ions is calcium chloride, but the person skilled in the art can select many other suitable sources of calcium ions.

In one embodiment, the source of calcium is calcium chloride. Suitably the calcium chloride solution has a concentration of about 1M.

When discussing the solubility of a composition herein, it is meant solubility at 25° C. (and otherwise standard conditions) in the relevant liquid medium used in the method. Typically, this medium will be aqueous, and in some cases will be water. It will be appreciated that the solubility of a given composition will vary depending on the relevant medium being used, e.g. depending on its polarity, but in the context that is entirely appropriate as the compositions such as calcium or phosphate salts are preferably soluble in the relevant medium being used. However, given that in the compositions of the present invention the medium is typically aqueous, it may be more convenient and simpler to define the solubility in terms of solubility in water. Accordingly, solubility of the source of calcium ions is suitably of 5 g per 100 ml of water or higher, 10 g per 100 ml of water or higher, or 50 g per 100 ml of water or higher.

Phosphate and Source of Phosphate:

In some embodiments, the compositions of the invention may comprise phosphate or a source of phosphate. In some embodiments, the compositions of the invention do not comprise additional phosphate or an additional source of phosphate.

By 'additional' phosphate or source of phosphate it is meant that the composition does not comprise any phosphate or source of phosphate other than the phosphopeptide and optionally monofluorophosphate of the composition.

Suitably, therefore, in one embodiment, the compositions do not comprise phosphate or a source of phosphate other than phosphorylated OPN and/or monofluorophosphate.

Therefore, in one embodiment, the composition of the invention or for use in the invention comprises a phosphopeptide and optionally monofluorophosphate, and does not comprise additional phosphate or an additional source of phosphate. Typical additional sources of phosphate may comprise phosphate buffers, suitably these are not present in the compositions.

In some embodiments, the compositions of the invention do not comprise additional phosphate ions or an additional source of phosphate ions. In some embodiments, the compositions of the invention do not comprise additional free phosphate. In some embodiments, the compositions of the invention do not comprise any exogenous free phosphate. In some embodiments, the compositions of the invention do not comprise additional free phosphate ions. In some embodiments, the compositions of the invention do not comprise exogenous free phosphate ions.

By 'exogenous' it is meant phosphate that is not derived from or comprised within a compound that is part of the compositions of the invention. Suitably it is meant phosphate that is not derived from or comprised within the phosphopeptide and optionally the monofluorophosphate of the compositions of the invention.

Suitably such compositions of the invention may be regarded as substantially phosphate-free. Suitably these compositions may comprise trace amounts of phosphate due to other components present in the composition, but suitably these compositions do not comprise any significant amount of phosphate, or a source of phosphate. Suitably, in particular, the compositions do not comprise phosphate buffers.

Suitably, therefore, the composition comprises a low amount of phosphate. Suitably a composition that does not comprise any significant amount of phosphate or a negligible amount of phosphate, for example, suitably comprises less than 15% w/w phosphate, suitably less than 14% w/w phosphate, suitably less than 13% w/w phosphate, suitably less than 12% w/w phosphate, suitably less than 11% w/w phosphate, suitably less than 10% w/w phosphate, suitably less than 9% w/w phosphate, suitably less than 8% w/w phosphate, suitably less than 7% w/w phosphate, suitably less than 6% w/w, suitably less than 5% w/w, suitably less than 4% w/w, suitably less than 3% w/w, suitably less than 2% w/w. In one embodiment, the compositions that do not comprise phosphate or a source of phosphate comprise less than 7% w/w phosphate. Suitably, as noted above, a negligible amount of phosphate may come from components of the compositions such as monofluorophosphate and the phosphopeptide such as phosphorylated OPN.

Suitably a composition that does not comprise additional phosphate or an additional source of phosphate comprises less than 100 mM, less than 90 mM, less than 80 mM, less than 70 mM, less than 60 mM, less than 55 mM, less than 50 mM, less than 45 mM, less than 40 mM, less than 35 mM, less than 30 mM, less than 25 mM, less than 20 mM, less than 15 mM phosphate, less than 10 mM phosphate, less than 5 mM phosphate. Suitably a composition that does not comprise additional phosphate or an additional source of phosphate comprises less than 49 mM phosphate. Suitably a composition that does not comprise additional phosphate or an additional source of phosphate comprises less than 23 mM phosphate.

Suitably the concentration of phosphate in the composition is determined by the Smillie calculation based on the degree of phosphorylation of any compounds in the composition. An exemplary calculation of the concentration of phosphate in a composition comprising phosphopeptide and monofluorophosphate according to the preferred embodiments of the invention is as follows:

An example of using the Smillie Equation to calculate the total concentration of phosphate in a composition (e.g. Toothboost) is as follows:

3% OPN=30 g/L

7% phosphorylation of OPN=2.1 g phosphate

Molecular weight of phosphate=94.97 g/mol $$\frac{1\ \mathrm{M}}{94.97\ \mathrm{g}} \times 2.1\ \mathrm{g} = 0.022\ \mathrm{M}$$

Also, 3.8 g MFP in 1 L ToothBoost

Molecular weight of MFP=143.95 g/mol $$\frac{1\ \mathrm{M}}{143.95\ \mathrm{g}} \times 3.8\ \mathrm{g} = 0.02639\ \mathrm{M}$$

Total phosphate concentration is 0.022 M+0.02639 M=48.39 mM

In one embodiment, a composition that does not comprise additional phosphate or an additional source of phosphate comprises less than 48.5 mM phosphate. Suitably in such an embodiment, the composition still comprises a phosphopeptide and monofluorophosphate. Suitably the composition comprises about 3% w/w phosphorylated OPN.

In one embodiment, a composition that does not comprise additional phosphate or an additional source of phosphate comprises less than 22.5 mM phosphate. Suitably in such an embodiment, the composition still comprises a phosphopeptide, but does not comprise monofluorophosphate. Suitably the composition comprises about 3% w/w phosphorylated OPN.

Suitably the compositions for treating or preventing dental hypersensitivity or xerostomia may optionally comprise additional phosphate or an additional source of phosphate. Suitably, therefore, in any of the aspects described herein, the composition may comprise phosphate or a source of phosphate. However, in some embodiments, such compositions may not comprise additional phosphate or an additional source of phosphate.

'Phosphate' and a 'source of phosphate' as used herein refers to any suitable source of phosphate ions. If present in the composition, the source of phosphate ions should be able to dissolve in a liquid medium to release phosphate ions. Suitably the source of phosphate ions may be a soluble phosphate salt. Suitably the source of phosphate ions has a solubility of 5 g per 100 ml of liquid medium or higher, 10 g per 100 ml of liquid medium or higher, 50 g per 100 ml of liquid medium or higher. The source of phosphate ions can be provided in solid form or be dissolved in a suitable liquid.

One particularly suitable source of phosphate ions is sodium phosphate (e.g. disodium hydrogen phosphate and/or trisodium phosphate), but the person skilled in the art can select many other suitable sources of phosphate ions.

As discussed above, given that in the compositions of the present invention the medium is typically aqueous, it may be more convenient and simple to define the solubility in terms of solubility in water. Accordingly, solubility of the source of phosphate ions is suitably of 5 g per 100 ml of water or higher, 10 g per 100 ml of water or higher, or 50 g per 100 ml of water or higher.

Fluoride and Sources of Fluoride:

The compositions of the invention may comprise fluoride or a source of fluoride.

Suitably the composition for prevention or treatment of dental hypersensitivity, preferably dentine hypersensitivity may comprise fluoride. Suitably the composition for the prevention or treatment of xerostomia may comprise fluoride. Suitably the composition for the prevention or treatment of demineralisation of an oral surface, dental caries and/or candidiasis infection in patients having xerostomia may comprise fluoride. Suitably, the composition for use in a method of treating or preventing dental hypersensitivity may comprise fluoride. Suitably, the composition for use in a method of treating or preventing xerostomia may comprise fluoride. Suitably, the composition for use in a method of treating or preventing demineralisation of an oral surface, dental caries and/or candidiasis infection in subject having xerostomia, may comprise fluoride. Suitably, the composition for use in a method of maintaining enamel mineral density in a subject having hypersensitivity and/or xerostomia may comprise fluoride. However, in some embodiments of the uses and methods described herein, the composition does not comprise fluoride or a source of fluoride.

Fluoride and sources of fluoride as used herein refers to any suitable source of fluoride ions. A source of fluoride ions should be able to dissolve in the liquid medium to release fluoride ions. Suitably the source of fluoride ions may be a soluble fluoride salt. Suitably the source of fluoride ions has a solubility of 5 g per 100 ml of liquid medium or higher, 10 g per 100 ml of liquid medium or higher, or 50 g per 100 ml of liquid medium or higher. The source of fluoride ions can be provided in solid form or be dissolved in a suitable liquid.

Suitable sources of fluoride ions are sodium fluoride, tin fluoride, calcium fluoride, and monofluorophosphate, but the person skilled in the art can select many other suitable sources of fluoride ions.

In one embodiment, the source of fluoride is monofluorophosphate.

As discussed above, given that in the compositions of the present invention the medium is typically aqueous, it may be more convenient and simple to define the solubility in terms of solubility in water. Accordingly, solubility of the source of fluoride ions is suitably of 5 g per 100 ml of water or higher, 10 g per 100 ml of water or higher, or 50 g per 100 ml of water or higher.

In some embodiments, the compositions of the invention do not comprise fluoride or a source of fluoride. In some embodiments, the compositions of the invention do not comprise fluoride. Suitably such compositions of the invention may be regarded as substantially fluoride-free. Suitably, these compositions may comprise trace amounts of fluoride due to other components present in the composition, but suitably these compositions do not comprise any significant amount of fluoride, or a source of fluoride. Suitably fluoride-free compositions are regarded as those having a negligible amount of fluoride, suitably less than 1% w/w fluoride or a source of fluoride, suitably less than 0.9% w/w, suitably less than 0.8% w/w, suitably less than 0.7% w/w, suitably less than 0.6% w/w, suitably less than 0.5% w/w, suitably less than 0.4% w/w, suitably less than 0.3% w/w, suitably less than 0.2% w/w, suitably less than 0.1% w/w. In one embodiment, the compositions that do not comprise fluoride or a source of fluoride comprise less than 0.1% w/w fluoride.

In some embodiments, the compositions of the invention do not comprise monofluorophosphate. Suitably, in some embodiments, the composition is a liquid. Suitably, the composition may be a 'MOL' or 'MOK' composition as described elsewhere herein. Suitably, in some embodiments, the composition is a colloid or paste. Suitably, the composition may be a 'MON' composition as described elsewhere herein. Suitably, in some embodiments, the composition is a gel. Suitably, the composition may be a 'MOL', 'MOK' or 'MON' composition.

Oral Surface:

The compositions of the present invention may be applied to an oral surface. Suitably the composition for use in prevention or treatment of dental hypersensitivity, preferably dentine hypersensitivity may be applied to an oral surface. Suitably the composition for use in the prevention or treatment of xerostomia may be applied to an oral surface. Suitably the composition for use in the prevention or treatment of demineralisation, dental caries and/or candidiasis infection in patients having xerostomia may be applied to an oral surface. Suitably the composition for use in the retention of mineral density in patients having hypersensitivity or xerostomia may be applied to an oral surface. Suitably, the composition for use in any methods as described herein may be applied to an oral surface.

Suitably the oral surface is a natural surface or a synthetic surface. Suitably the oral surface may be a hard surface or a soft surface. Suitably the hard surfaces may be natural or synthetic. Suitably the soft surfaces may be natural or synthetic.

Suitable hard surfaces include teeth, dentures, veneers and the like. Suitably the hard surfaces are mineralised. Suitable hard mineralised surfaces include enamel, dentine or cementum. Suitably the soft surfaces are not mineralised. Suitable soft surfaces include gums, or tongue.

Suitable natural surfaces include teeth, gums, tongue. Suitably the synthetic surfaces include oral appliances, or oral accessories and prosthesis. Suitable synthetic surfaces may be formed of plastics or metal. Suitably oral accessories may include dentures, veneers, bridges, aligners and the like.

Suitably in any aspect of the present invention, the oral surface is a natural oral surface. In an embodiment for use in prevention or treatment of dental hypersensitivity, suitably the oral surface is teeth, specifically the surface of teeth, more specifically the dentine of teeth. In an embodiment for use in prevention or treatment of xerostomia, or candidiasis in xerostomia, suitably the oral surface is the tongue and gums. In an embodiment for use in prevention or treatment of demineralisation or dental caries, suitably the oral surface is teeth, specifically the surface of teeth, more specifically the enamel of teeth or dentine of teeth. In an embodiment for use in maintaining enamel mineral density, suitably the oral surface is teeth, specifically the surface of teeth, more specifically the enamel of teeth. In one embodiment, the composition is for use in maintaining dentine mineral density. Suitably, in some embodiments, the composition is for use in maintaining enamel mineral density and dentine mineral density.

Suitably the oral surface may be located within a mouth. Suitably within a mouth of a subject. Suitably the subject may be a human or animal. Suitably therefore the uses and methods of the invention may be performed on a human or animal subject. In one embodiment, the subject is a human. In one embodiment, the subject is a domestic animal, such as a cat or a dog.

Suitably, the uses and methods of the invention as described herein may comprise applying the compositions of the invention to an oral surface. Suitably applying the compositions of the invention to an oral surface may comprise administering the composition to the mouth of a subject. Suitably administering the composition to the mouth of a subject contacts the oral surfaces located within the mouth of the subject with the composition. Suitable programs of administration are described herein below.

Dental Hypersensitivity

Some aspects of the present invention relate to use of compositions and methods for the prevention or treatment of dental hypersensitivity.

Suitably, in some embodiments dental hypersensitivity is dentine hypersensitivity. In some embodiments, dental hypersensitivity is associated with gum recession, abfraction, over-brushing, enamel erosion, periodontal disease, orthodontics and/or tooth whitening. Some embodiments of the present invention relate to use of compositions for the maintenance of enamel mineral density in patients having hypersensitivity. Suitably, in some embodiments the composition is for use in the prevention or treatment of hypersensitivity by preventing or reducing enamel erosion.

By 'associated with' it is meant that the dental hypersensitivity may be directly or indirectly caused by the listed conditions in a patient, or may be present concurrently with the listed conditions in a patient, or may be predicted or expected to occur in a patient having one or more of the listed conditions.

Suitably therefore, the present invention may relate to the use of compositions and methods for the prevention or treatment of dental hypersensitivity in patients having one or more of the following: gum recession, abfraction, over-brushing, enamel erosion, periodontal disease, orthodontics and/or tooth whitening.

Suitably, in aspects where the composition is for use in the prevention or treatment of dental hypersensitivity the composition is administered after eating or drinking. In some embodiments the composition may be administered immediately after eating or drinking. In another embodiment, the composition may be administered within 2 hours after eating or drinking. Suitably, in some embodiment the composition is administered within 1 hour, within 30 minutes, within 15 minutes, within 10 minutes, within 5 minutes, within 2 minutes, within 1 minute after eating or drinking. In some embodiments, the composition is for administration during the day or night. Suitably the composition is for administration to the mouth of a subject.

In some embodiments, the composition is used as an adjunct to regular oral care routines, suitably therefore the composition is for use in combination with other oral care products or compositions.

In some embodiments, the composition provides relief from hypersensitivity for a least 1 day, at least 1.5 days, at least 2 days or at least 3 days.

Suitably, in some embodiments, the composition provides fresh breath. In one embodiment, the composition may remove an aftertaste following eating or drinking.

Suitably, in aspects where the composition is for use in the prevention or treatment of dental hypersensitivity the composition is a colloid or paste formulation. In some embodiments, the composition may be MON.

Suitably, in aspects where the composition is for use in the prevention or treatment of dental hypersensitivity the composition is a liquid formulation. In some embodiments, the composition may be MOL or MOK.

Suitably, in aspects where the composition is for use in the prevention or treatment of dental hypersensitivity or methods thereof the composition is a gel formulation. In some embodiments, the composition may be 'MOL', 'MOK' or 'MON'.

Xerostomia

Some aspects of the present invention relate to use of compositions and methods for the prevention or treatment of xerostomia or dry mouth. Some aspects of the present invention relate to use of compositions for the prevention or treatment of demineralisation of an oral surface, dental caries and/or candidiasis infection in patients having xerostomia. Some aspects of the present invention relate to use of compositions for the maintenance of enamel mineral density in patients having xerostomia. Suitably, some aspects of the invention relate to the use of compositions in methods of preventing or treating xerostomia related conditions.

Suitably, in some embodiments xerostomia is associated with Sjögren's Syndrome, cancer treatment, polypharma, and/or diseases of the salivary glands.

By 'associated with' it is meant that the xerostomia may be directly or indirectly caused by the listed conditions in a patient, or may be present concurrently with the listed conditions in a patient, or may be predicted or expected to occur in a patient having one or more of the listed conditions.

Suitably therefore, the present invention may relate to the use of compositions for the prevention or treatment of xerostomia in patients having one or more of the following: Sjögren's Syndrome, cancer, polypharma, and/or diseases of the salivary glands.

Suitably, some embodiments relate to a composition for use in the prevention or treatment of xerostomia induced demineralisation of an oral surface, dental caries and/or candidiasis infection. In some embodiments, xerostomia induced demineralisation of an oral surface, dental caries and/or candidiasis infection are considered xerostomia related conditions.

By 'induced' it is meant that the demineralisation of an oral surface, dental caries and/or candidiasis infection are caused directly or indirectly by xerostomia, suitably directly caused by xerostomia in a patient.

Suitably, where the composition is for use in the prevention or treatment of xerostomia, patients having xerostomia, or conditions induced thereby, the composition may be administered in the evening or at night, and/or after eating or drinking. In some embodiments, the composition is for use in a method of preventing or treating xerostomia, patients having xerostomia, or conditions induced thereby, wherein the composition may be administered in the evening or at night, and/or after eating or drinking. In some embodiments, the composition may be administered prior to sleep to prevent or treat demineralisation or dental caries induced by xerostomia or in patients having xerostomia. Suitably administration prior to sleep increases the buffering capacity of saliva as explained elsewhere herein. Suitably the composition is for administration to the mouth of a subject.

In some embodiments, the composition is for use in preventing or treating xerostomia by increasing the buffering capacity of saliva. In some embodiments the composition is for use in preventing or treating xerostomia induced demineralisation of an oral surface, dental caries and/or candidiasis infection by increasing the buffering capacity of saliva. In some embodiments, there is provided a method of treating or preventing xerostomia by increasing the buffering capacity of saliva in a subject in need thereof, wherein the method comprises administering to the subject a therapeutically effective amount of a composition comprising a phosphopeptide. In another embodiment, there is provided a method of treating or preventing xerostomia induced demineralisation of an oral surface, dental caries and/or candidiasis infection by increasing the buffering capacity of saliva in a subject in need thereof, wherein the method comprises administering to the subject a therapeutically effective amount of a composition comprising a phosphopeptide.

Suitably the compositions increase the buffering capacity of saliva by at least 1×, at least 1.25×, at least 1.5×, at least 1.75×, at least 2×, at least 2.25×, at least 2.5 or at least 3× relative to saliva from an individual that has not received a composition of the invention.

By 'buffering capacity' it is meant the ability of saliva to buffer against changes in pH caused by acidic foods and bacterial action. Buffering capacity may be defined as the resistance to change of pH of a solution containing a buffering agent. Buffering capacity is the concentration of protons required to shift the pH of a solution 1 unit either side of the pKa $H^+$/(L saliva*pH unit).

Suitably the composition increase the buffering capacity of saliva by at least 1×, at least 1.25×, at least 1.5×, at least 1.75×, at least 2×, at least 2.25×, at least 2.5 or at least 3× relative to saliva from a subject that has not received a composition of the invention. Suitably the subject that has not received the composition is a healthy subject.

Suitably the composition increase the buffering capacity of saliva to a desired healthy level, suitably between about 5 to 9 $H^+$/(L saliva*pH unit), suitably about 5.5 to 8.5 $H^+$/(L saliva*pH unit), suitably about 6 to 8 $H^+$/(L saliva*pH unit), suitably about 6.5 to 7.5 $H^+$/(L saliva*pH unit), suitably about 7.25 mM $H^+$/(L saliva*pH unit).

Suitably the composition may maintain the buffering capacity of saliva at a desired healthy level, suitably between about 5 to 9 $H^+$/(L saliva*pH unit), suitably about 5.5 to 8.5 $H^+$/(L saliva*pH unit), suitably about 6 to 8 $H^+$/(L saliva*pH unit), suitably about 6.5 to 7.5 $H^+$/(L saliva*pH unit), suitably about 7.25 mM $H^+$/(L saliva*pH unit).

In some embodiments, the composition is used as an adjunct to regular oral care routines, suitably therefore the composition is for use in combination with other oral care products or compositions.

In some embodiments, the composition provides enhanced lubrication and/or improved mouth feel. Suitably, in one embodiment the composition prevents lips sticking to teeth.

In some embodiments, the composition provides relief from xerostomia for at least 1 day, at least 1.5 days, at least 2 days, at least 3 days.

Suitably, in some embodiments, the composition provides fresh breath. In one embodiment, the composition may remove an aftertaste following eating or drinking.

Suitably, in aspects where the composition is for use in the prevention or treatment of xerostomia the composition is a liquid formulation. In some embodiments, the composition may be MOL or MOK.

Therapy and Related Methods

Some aspects of the invention relate to methods of treatment or prevention of hypersensitivity or xerostomia in a subject in need thereof, wherein the method comprises administering to said subject a therapeutically effective amount of a composition as described herein. In one aspect of the present invention there is provided a method of treatment or prevention of demineralisation of an oral surface, dental caries and/or candidiasis infection in subject having xerostomia, wherein the method comprises administering to said subject a therapeutically effective amount of a composition as described herein.

In a further aspect of the present invention there is provided a method of maintaining enamel mineral density in a subject having hypersensitivity and/or xerostomia, wherein the method comprises administering to said subject a therapeutically effective amount of a composition as described herein. In another embodiment, there is provided a method of maintaining dentine mineral density in a subject having hypersensitivity and/or xerostomia, wherein the method comprises administering to said subject a therapeutically effective amount of a composition as described herein. Suitably, in such embodiments, mineral density is maintained by remineralisation or by preventing demineralisation.

'Therapeutically effective amount' as used herein may refer to any amount of the composition that results in preventing, delaying or ameliorating symptoms associated with the conditions described herein. In some embodiments of the methods as described herein, the method comprises administering a therapeutically effective amount of the composition to an oral surface. Suitably, in some embodiments, the composition is administered directly to the tooth surface in a subject in need thereof. In an alternative embodiment, the composition is applied to the oral cavity of a subject in need thereof.

In some embodiments of the methods or uses as described herein, the composition may be administered in combination with other oral care products or compositions. In combination with as used herein may refer to administering a composition of the present invention as an adjunct to other oral care products or compositions. Suitably, the methods as described herein may be performed as an adjunct to regular oral care routines.

Administration

In any aspects of the invention as described herein, the composition is suitably administered to the mouth of a subject in need thereof.

In some embodiments, the composition is administered to the subject for at least 5 days, at least 6 days, at least 7 days, at least 8 days, at least 9 days, at least 10 days, at least 11 days, at least 12 days, at least 13 days, at least 14 days, at least 15 days, suitably consecutively. In some aspects, the composition is administered to the subject at least once a day, at least twice a day, at least three times a day. In some aspects, the composition is administered to the mouth of the subject at least once a day, at least twice a day, at least three times a day. In some embodiments of the invention, the composition is administered once or twice a day for at least 5 days.

Suitably, the composition may be administered to the mouth of a subject after eating or drinking. In some embodiments the composition may be administered immediately after eating or drinking. In another embodiment, the composition may be administered within 2 hours after eating or drinking. Suitably, in some embodiment the composition is administered within 1 hour, within 30 minutes, within 15 minutes, within 10 minutes, within 5 minutes, within 2 minutes, within 1 minute after eating or drinking.

Suitably, the composition may be administered during the day or night. In some embodiments, the composition is administered prior to sleeping. Suitable specific administration routines are discussed in the relevant sections hereinabove.

In some embodiments, the composition is used as an adjunct to regular oral care routines.

In some embodiments, the composition may be administered as a spray. Suitably, the spray may be applied directly on to an oral surface. In another embodiment, the composition may be administered as mouth wash.

In another embodiment, the composition may be administered as a gel or a paste. Suitably, in some embodiments the gel or paste is applied directly to an oral surface. In one embodiment, the gel or paste is administered using a pen delivery system. Alternatively, in another embodiment the gel or paste is administered in an aligner tray. Suitably, in some embodiments, the composition may be MOK or MOL or MON. In a preferred embodiment, the gel composition is MOK.

Suitably, in some embodiments, the composition is administered before or after administration of other oral care products or compositions. Suitably, in some embodiments the composition is administered before or after brushing with a toothpaste. In some embodiments, the composition is administered at least 5 minutes, at least 10 minutes, at least 15 minutes, at least 30 minutes, at least 1 hour, at least 2 hours, at least 3 hours, at least 4 hours, at least 5 hours or at least 6 hours, at least 7 hours, at least 8 hours, at least 9 hours, at least 10 hours, at least 11 hours or at least 12 hours prior to brushing with a toothpaste. Alternatively, in another embodiment, the composition is administered at least 5 minutes, at least 10 minutes, at least 15 minutes, at least 20 minutes, at least 30 minutes, at least 1 hour, at least 2 hours, at least 3 hours, at least 4 hours, at least 5 hours, at least 6 hours, at least 7 hours, at least 8 hours, at least 9 hours, at least 10 hours, at least 11 hours or at least 12 hours after brushing with a toothpaste.

It may be desirable in some embodiments to administer the composition to the mouth before or after brushing with a toothpaste comprising at least 1000 ppm; at least 1100 ppm; at least 1200 ppm; at least 1300 ppm; at least 1350 ppm; at least 14000; at least 1450 ppm or at least 1500 ppm or at least 2,500 ppm or at least 5,000 ppm of fluoride. In a preferred embodiment, the composition is administered after brushing with a toothpaste comprising at least 1100 ppm fluoride.

Alternatively, in some embodiments, the composition is administered before or after brushing with a low fluoride or fluoride free toothpaste. Low fluoride toothpaste may include toothpastes with 1100 ppm or less, 1000 ppm or less, 900 ppm or less, 800 ppm or less, 700 ppm or less, 600 ppm or less, 500 ppm or less, 400 ppm or less, 300 ppm or less, 200 ppm or less fluoride. Fluoride free toothpaste includes any toothpastes with a maximum of 150 ppm fluoride. Suitably, where the composition is administered before or after brushing with a low fluoride or fluoride free toothpaste, it may be desirable in some embodiments that the composition further comprises fluoride or a source of fluoride, such as, but not limited to, monofluorophosphate. Without wishing to be bound by theory, it is believed that the addition of fluoride to the composition may provide additional benefits such as antimicrobial activity.

Packaging

In an aspect of the present invention there is provided packaging comprising a composition for use according any of the aspects of the invention.

Suitably the packaging contains the composition for use of the invention. Suitably the packaging may also be operable to deliver the composition for use of the invention, suitably to an oral surface. Suitably the packaging may comprise a container to contain the composition for use. Suitably the packaging may further comprise an applicator or an actuator.

Suitably the packaging may comprise an actuator. Suitably upon actuation of the actuator, the composition is expelled from the packaging, suitably from within the container of the packaging. Suitably, the actuator is operable to deliver a metered dose of the composition when actuated. Suitably a metered dose is a suitable amount of the composition to achieve the desired effect. Suitably a metered dose is an amount suitable for a mouth of a subject, for example between 0.1 ml up to 5 ml.

Suitable actuators may include a spray nozzle. Suitably, upon actuation of the spray nozzle, droplets of the composition are expelled from the packaging.

Suitably the packaging may further comprises a propellant, suitably the propellant aids expelling the composition from the packaging. Suitably, in such an embodiment, the spray nozzle is an aerosolization spray nozzle.

In one embodiment, the packaging comprises a spray nozzle. Suitably, in such an embodiment, the packaging may be termed a ‘spray pack’. Suitably, in such an embodiment, the composition is an oral spray.

Embodiments of the present invention will now be described, by way of non-limiting example, with reference to the accompanying drawings.

DETAILED DESCRIPTION OF EMBODIMENTS OF THE INVENTION AND EXAMPLES

Figure 1:
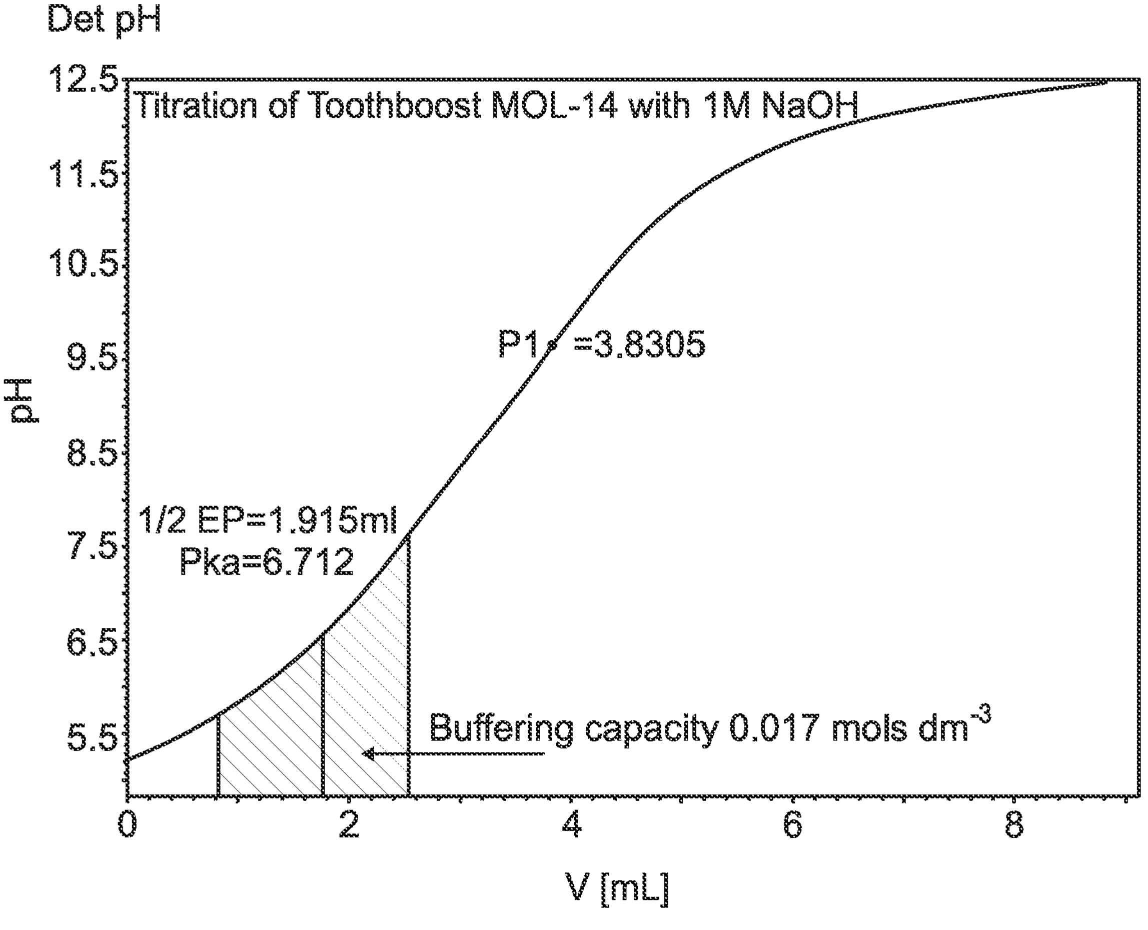
FIG. 1: The titration of Toothboost with sodium hydroxide showing the end point, Pka and buffering capacity at ½ EP+/−1 pH unit.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The term 'about' as used herein may refer to +/−20%, +/−15%, or +/−10% of the value recited, suitably +/−10% of the value recited.

The term 'treatment' or 'treating' as used herein may refer to reducing, ameliorating or eliminating one or more signs, symptoms, or effects of a disease or condition. 'Treatment' as used herein includes any treatment of a disease in a mammal, particularly a human, and includes: (a) preventing the disease from occurring in a subject predisposed to the disease or at risk of acquiring the disease but has not yet been diagnosed as having it; (b) inhibiting the disease, i.e., arresting its development; and (c) relieving the disease, i.e., causing regression of the disease.

The term 'prevention' or 'preventing' as used herein may refer to stopping, inhibiting or reducing one or more signs, symptoms, or effects of a disease or condition. 'Prevention' as used herein includes: (a) avoiding the disease from occurring in a subject predisposed to the disease or at risk of acquiring the disease but has not yet been diagnosed as having it; (b) inhibiting the disease, i.e., arresting its development.

The term 'maintaining mineral density' as used herein may refer to stopping, inhibiting or reducing demineralisation of dental enamel or dentine, or both enamel and dentine. Suitably, maintaining mineral density may also refer to remineralisation. The term remineralisation as used herein may refer to mineral deposits made on to the oral surface. Suitably prevention of demineralisation as used herein may mean that the oral surface is protected from loss of minerals. The term 'maintaining enamel mineral density' as used herein may refer to stopping, inhibiting or reducing demineralisation of dental enamel. The term 'maintaining dentine mineral density' as used herein may refer to stopping, inhibiting or reducing demineralisation of dentine mineral density.

The term 'administering' or 'administration' as used herein may refer to introducing or delivering to a subject the composition by any route to perform its intended function.

The term 'subject' or 'subject in need thereof' as used herein may be used interchangeably with 'individual' or 'patient', and refer to any individual subject with a disease or condition in need of prevention or treatment unless otherwise stated. For the purposes of the present disclosure, the subject may be a mammal, preferably a human.

The term "Toothboost" is used herein at some points in the examples to describe liquid compositions according to the present invention such as 'MOK' as prepared in example 1 or 'MOL' as prepared in example 2. 'MOK' refers to a liquid formulation containing phosphate in the form of phosphate buffers.

The term "Boostpaste" is used herein at some points in the examples to describe paste compositions according to the present invention such as 'MON' as prepared in example 2.

Example 1—Liquid Composition Comprising Phosphoproteins and Phosphate—"MOK"

The formulation of MOK is as follows:

| MOK batches | |
|---|---|
| Intermediate A<br>Ingredient | % w/w |
| Sodium Methyl Paraben | 0.2-0.3, e.g. 0.26 |
| Phenoxyethanol | 2.6 |
| Saccharine | 1.0 |
| Tego Betain | 7.7 |
| Deionised water | 81.5 |
| Flavour oil | 7.0 |

| Finished Product<br>Ingredient | % w/w |
|---|---|
| OPN-10 | 3.0 |
| Trisodium phosphate 0.1M solution | 16.0 |
| Disodium hydrogen phosphate 0.1M solution | 16.0 |
| Sodium bicarbonate 1M solution | 15.0 |
| Deionised water | 30.0 |
| calcium chloride 1M solution | 2.9 |
| Monofluorophosphate | 0.4 |
| xylitol | 5.0 |
| Intermediate A | 7.7 |
| make up to volume after final pH adjustment | 4.0 |

To make the Intermediate A flavour system:

1. Mix Phenoxyethanol with flavour oil.
2. Disperse Tego Betain into the solution by mixing.
3. Mix saccharin, methyl paraben and the deionised water until a clear solution.
4. Add this quickly to the tego betain suspension and stir. After about an hour it is a clear straw colour solution.

To make the finished product:

1. Add ⅔ of the total volume of deionised water to 3.0% w/w OPN-10 and rapidly mix for two hours until the solution clears.
2. Add 1M calcium chloride at a rate of 0.3 ml/min with rapid stirring.
3. Add tri-sodium phosphate and di-sodium hydrogen phosphate to the OPN-10 solution at a rate of 0.4/min.

4. Add monofluorophosphate solution made from dissolving MFP into ⅓ of the total volume of deionised water. Add back to the OPN solution at a rate of 0.2 ml/min. This will result in a very slightly cloudy pale yellow/white solution.
5. Add the sodium bicarbonate solution at a rate of 0.3 ml/min, keeping pH at 7.5±0.3 with 1M HCl/1M NaOH.
6. Add intermediate A to the OPN solution at a rate of 0.2 ml/min with rapid stirring.

This will result in a clear solution.

7. Mix in 5.0% w/w xylitol.
8. Adjust the pH of the solution to 7.5.
9. Make up to 100.0 g with deionised water.
10. After 24H Filter through a 0.22 um sterile filter.

If using a single transfer tube for the reagents, it must be washed through before each reagent is added.

Example 2—Liquid Composition Comprising Phosphoproteins (Phosphate Free)—"MOL"

MOL batches Fluoride free.

| Ingredient | % w/w |
|---|---|
| Intermediate A | |
| Sodium Methyl Paraben | 0.2-0.3, e.g. 0.26 |
| Phenoxyethanol | 2.6 |
| Saccharine | 1.0 |
| Tego Betain | 7.6 |
| Deionised water | 81.5 |
| Flavour oil | 6.9 |
| Finished Product | |
| OPN-10 | 3.0 |
| Sodium bicarbonate 1M solution | 15.0 |
| Deionised water. | 54.0 |
| Calcium chloride 1M solution | 2.9 |
| Xylitol | 5.0 |
| HCl 1M solution | 11.0 |
| Intermediate A | 7.7 |
| Make up to final volume with water after final pH adjustment | 1.4 |

MOL batches with fluoride

| Ingredient | % w/w |
|---|---|
| Intermediate A | |
| Sodium Methyl Paraben | 0.2-0.3, e.g. 0.26 |
| Phenoxyethanol | 2.6 |
| Saccharine | 1.0 |
| Tego Betain | 7.6 |
| Deionised water | 81.5 |
| Flavour oil | 6.9 |
| Finished Product | |
| OPN-10 | 3.0 |
| Sodium bicarbonate 1M solution | 15.0 |
| Deionised water. | 54.0 |
| Monofluorophosphate | 0.4 |
| Calcium chloride 1M solution | 2.9 |
| Xylitol | 5.0 |
| HCl 1M solution | 11.0 |
| Intermediate A | 7.7 |
| Make up to final volume with water after final pH adjustment | 1.0 |

Manufacture of flavour system Intermediate A.

1. Mix Phenoxyethanol with flavour oil.
2. When a clear solution, disperse Tego Betain into the solution and mix until fully dispersed.
3. Mix saccharin and methyl paraben to deionised water and mix until dissolved.
4. Add the saccharine mix, quickly, to the tego suspension and stir. After about an hour it is a clear straw colour solution.

Manufacture of finished product (100 g).

1. Add 49 g of deionised water to a beaker and add 3.0 g of OPN and stir for two hours.
2. Add calcium solution.
3. Mix MFP with 5 ml of deionised water and add to bicarbonate solution and add xylitol and stir until dissolved.
4. Add sodium bicarbonate.
5. Add Intermediate A.
6. Add HCl solution.
7. Check and adjust pH after 24 hours.
8. Filter through a 0.2 μm sterile filter.

A phosphate free and fluoride free formulation of MOL can be made in the same way as detailed above with the same components except monofluorophosphate (MFP) is not included, see above Table.

Example 3—Paste Composition Comprising Phosphoproteins (Phosphate Free)—"MON"

MON batches Fluoride free

| Intermediate A | % w/w |
|---|---|
| Sodium Methyl Paraben | 0.2-0.3, e.g. 0.26 |
| Phenoxyethanol | 2.6 |
| Saccharine | 1.0 |
| Tego Betain | 7.6 |
| Deionised water | 80.7 |
| Flavour oil | 7.8 |

| Finished product Ingredient | % w/w |
|---|---|
| OPN-10 | 3.0 |
| Sodium bicarbonate | 2.0 |
| Zeofree 153 | 12.0 |
| Abrasive silica | 6.0 |
| Deionised water. | 22.9 |
| HCl 1M | 34.0 |
| Calcium chloride solid | 0.5 |
| Manitol | 9.0 |
| Xanthan | 0.8 |
| Intermediate A | 7.7 |
| make up to with water after final pH adjustment | 2.1 |

| MON batches with Fluoride | |
|---|---|
| Intermediate A | % w/w |
| Sodium Methyl Paraben | 0.2-0.3, e.g. 0.26 |
| Phenoxyethanol | 2.6 |
| Saccharine | 1.0 |
| Tego Betain | 7.6 |
| Deionised water | 80.7 |
| Flavour oil | 7.8 |

| Finished product Ingredient | % w/w |
|---|---|
| OPN-10 | 3.0 |
| Sodium bicarbonate | 2.0 |
| Zeofree 153 | 12.0 |
| Abrasive silica | 6.0 |
| Deionised water. | 22.9 |
| HCl 1M | 34.0 |
| Calcium chloride solid | 0.5 |
| Monofluorophosphate | 1.1 |
| Manitol | 9.0 |
| Xanthan | 0.8 |
| Intermediate A | 7.7 |
| make up to with water after final pH adjustment | 1.0 |

Manufacture of flavour system Intermediate A.

1. Mix Phenoxyethanol with flavour oil.
2. When a clear solution, disperse Tego Betain into the solution and mix until fully dispersed.
3. Mix saccharin and methyl paraben to deionised water and mix until dissolved.
4. Add the saccharine mix, quickly, to the tego suspension and stir. After about an hour it is a clear straw colour solution.

Manufacture of finished product (100 g).

1. Add deionised water and 1M HCl and OPN and stir for 30 min.
2. Add sodium bicarbonate, calcium, Zeofree silica and Abrasive silica, MFP and Manitol.
3. Mix with a high sheer mixer until fully dispersed.
4. Add Intermediate A.
5. Mix in Xanthan.
6. Check pH by taking 2 g of the paste a make a 25% suspension. Adjust to 7.0, if required.

A phosphate free and fluoride free formulation of MON can be made in the same way as detailed above with the same components except monofluorophosphate (MFP) is not included, see above Table.

Example 4—Toothboost Oral Spray Consumer Trial A

Introduction: A consumer trial study to measure the effect of Toothboost Oral Spray containing the MOK formulation on sensory acceptability and usability of the oral spray. Participants pre-existing dental hypersensitivity was unknown prior to conducting the trial.

Method: Five volunteers were provided a 15 ml bottle of Toothboost Oral Spray containing Toothboost MOK formulation. Participants were instructed to apply the oral spray directly into the mouth after meals, snacks and drinks and to use as an adjunct to regular daily brushing routines. Additionally, participants were permitted to use the spray as a breath freshener. The participants used Toothboost Oral Spray for an average of 4-6 weeks, until the 15 ml bottle was finished.

The participants were then provided a trial questionnaire. The questionnaire comprised:

Section 1. 5 Likert Scale Questions to rate

Sensory experience—taste/flavour/mouth feel/after taste

Product visual—colour appearance

Product ease of use

Section 2. 7 Qualitative Questions to self-report on

Frequency and patterns of use

Effect of Toothboost oral spray on teeth/mouth

Recommend or purchase product

Results: The participant's scoring on the 5 Likert Scale Questions as shown in Table 1 demonstrates that three out of five participants rated the mouth feel, taste and after-taste as 100% satisfactory for these outcomes. Two of the five participants self-reported relief from dental hypersensitivity when using Toothboost Oral Spray. Two participants had a history of pre-existing dental hypersensitivity, which was unknown prior to taking part in the trial.

TABLE 1

| 5 Participants Ratings of Toothboost Product 1 to 5, 1 = Poor, 5 = Excellent | |
|---|---|
| Category | Score |
| Colour/Appearance | 4/5 5/5 5/5 5/5 5/5 |
| Taste Flavour | 5/5 5/5 5/5 4/5 4/5 |
| Texture/Mouth-feel | 5/5 5/5 4/5 5/5 4/5 |
| After-taste | 5/5 5/5 5/5 4/5 5/4 |
| Ease of use | 2/5 5/5 2/5 3/5 3/5 |

Example 5—Toothboost Oral Spray Consumer Trial B

Introduction: A consumer trial study to measure the effect of Toothboost Oral Spray containing the MOL formulation on sensory acceptability and usability of the oral spray. Participants pre-existing dental hypersensitivity was unknown prior to conducting the trial.

Method: Three volunteers were provided a 15 ml bottle of Toothboost Oral Spray containing Toothboost MOL formulation. Participants were instructed to apply the oral spray directly into the mouth after meals, snacks and drinks and use as an adjunct to regular daily brushing routines. Additionally, participants were permitted to use the spray as a breath freshener. The participants used Toothboost Oral Spray for an average of 4-6 weeks, until the 15 ml bottle was finished.

The participants were then provided a trial questionnaire. The questionnaire comprised:

Section 1. 5 Likert Scale Questions to rate

Sensory experience—taste/flavour/mouth feel/after taste

Product visual—colour appearance

Product ease of use

Section 2. 7 Qualitative Questions to self-report on

Frequency and patterns of use

Effect of Toothboost oral spray on teeth/mouth

Recommend or purchase product

Results: The participant's scoring on the 5 Likert Scale Questions as shown in Table 2 demonstrates that the participants highly rated all parameters tested. One of the three participants self-reported relief from dental hypersensitivity when using Toothboost Oral Spray. This participant had a pre-existing history of dental hypersensitivity, which was unknown prior to taking part in the trial. At follow up, the participant revealed that hypersensitivity returned within 1.5 days of stopping use of the Toothboost spray.

Further studies have revealed participants observing rapid and dramatic reduction in dental sensitivity associated with aligner use and minor tooth fractures. Benefits were typically observed within 3-4 days of use, and the reduction in sensitivity was reported as complete or near complete. This supports the high efficacy of compositions of the present invention in relieving dental hypersensitivity.

TABLE 1

3 Participants Ratings of Toothboost Product 1 to 5, 1 = Poor, 5 = Excellent

| Category | Score |
|---|---|
| Colour/Appearance | 4/5 5/5 5/5 |
| Taste Flavour | 4/5 4/5 4/5 |
| Texture/Mouth-feel | 4/5 5/5 5/5 |
| After-taste | 3/5 5/5 5/5 |
| Ease of use | 5/5 5/5 5/5 |

Example 6—Xerostomia Toothboost Oral Spray Consumer Trial

Introduction: One participant who took part in a Toothboost oral spray consumer trial B had a clinical diagnosis of Sjögren's Syndrome. The chief oral complaint of individuals with Sjögrens has been the symptom of xerostomia, associated with significant morbidity and affecting the oral-health-related quality of life of patients.

Method: The participant volunteered to take part in a consumer trial to provide feedback on the oral spray product relating to patterns of use, sensory experience and its effect on their dry mouth condition. The participant was given a 15 ml Toothboost Oral Spray MOL formulation sample and advised to use as an adjunct to regular daily brushing routines. The participant was instructed to apply the oral spray directly into the mouth after meals, snacks and drinks. The spray could also be used as a breath freshener.

Section 1. 5 Likert Scale Questions to rate

Sensory experience—taste/flavour/mouth feel/after taste

Product visual—colour appearance

Product ease of use

Section 2. 7 Qualitative Questions to self-report on

Frequency and patterns of use

Effect of Toothboost oral spray on teeth/mouth

Recommend or purchase product

Results: The participant's scoring on the 5 Likert Scale Questions as shown in Table 3 demonstrates 100% satisfaction for the tested outcomes. The participant provided additional comments that Toothboost provided relief from night time oral dryness and worked better than any other dry mouth products tried to date.

TABLE 3

1 Participant Rating of Toothboost Product 1 to 5, 1 = Poor, 5 = Excellent

| Category | Score |
|---|---|
| Colour/Appearance | 5/5 |
| Taste Flavour | 5/5 |
| Texture/Mouth-feel | 5/5 |
| After-taste | 5/5 |
| Ease of use | 5/5 |

Toothboost oral mist offers an on-the-go solution to address the clinical and sensory issues for patients and consumers experiencing dry mouth.

Example 7—Measurement of the Buffering Capacity of Toothboost MOL Formulation

Introduction: The average buffering capacity of saliva from healthy adult volunteers during the day is measured as 7.25 mM $H^+$/(L saliva*pH unit) (Archives of Oral Biology. Volume 45, Issue 1, January 2000, Pages 1-12). During sleep, the buffering capacity from bicarbonate buffer significantly drops and there have been extensive studies to show a correlation between saliva buffering capacity and prevalence of caries. Some have reported that a buffering capacity of 0.43 mM $H^+$/(L saliva*pH unit) corresponds to a rampant condition of caries.

Method: MOL Toothboost was titrated with 1M sodium hydroxide to end point. The Pka and buffering capacity at ½ end point+/−1 pH unit is then calculated as $H^+$/(L*pH unit).

Results: The pH titration of Toothboost shows an increase in the oral buffering capacity to 17.0 mM $H^+$/(L*pH unit). This equates to a 2.3× increase in the buffering capacity compared to human saliva alone. See FIG. 1 for a graph of the results. The treatment acts as a reservoir of Toothboost that further buffers the saliva against acidic pH when administered using the Toothboost misting technology.

Example 8—Measurement of Fluid Flow Though Human Dentine when Treated with Toothboost MOK-10 Formulation Introduction: Hypersensitivity is associated with an increased rate of fluid flow in the dentinal tubules and distortion of the dental nerve fibres causing pain. A hydraulic conductance study was performed to measure the reduction in fluid flow through human dentine when treated with Toothboost MOK-10 compared to 10% oxalic acid solution or deionised water over a 5 day treatment regime.

Methods:

(i) Specimen Preparation

Caries free human molars were sectioned and single dentine discs prepared. A single dentine disc of approximately 800 μm thickness was removed from between the crown and pulp cavity. The dentine discs were polished to 500 μm thickness and flattened on both sides of the disc. The discs were then placed into 1% w/w citric acid solution, pH 3.75 and sonicated for five minutes. The discs were rinsed with an excess volume of deionised water. Acceptance criteria for the initial flow rate of the discs is between 1.0-20.0 ul/min. After the baseline hydraulic conductance measurements were made, the discs were stratified into two groups of ten discs so that each group had a similar range of fluid flow rates.

(ii) Hydraulic Conductance Method to Measure Fluid Flow Rate

A solvent chamber of hydraulic conductance equipment was pressurised to 1.0 PSI. A dentine disc was placed into the split cell holding chamber and Earles solution passed through the system. The hydrodynamic flow rate through the dentine was then measured and recorded for five minutes.

(iii) Treatment Procedure

N=10 dentine discs were selected for each treatment group. An initial baseline flow rate through the dentine of each disc was measured using the hydraulic conductance method. The flow of Earles solution was turned off and excess liquid was removed from the dentine disc. The disc was treated with a single actuation of a mister spray with either Toothboost MOK-10, 10% oxalic acid solution as a positive control or deionised water as a negative control and incubated for 2 minutes. The dentine disc was then rinsed with deionised water and the flow of Earles solution switched on and the dentine flow rate measured. The split cell was then removed from the hydraulic conducting instrument and placed into a container with 50 ml of artificial saliva and incubated at 37° C. until the next treatment. The treatment was repeated five times spaced evenly over one day, for five consecutive days. Each day, the discs were removed from the artificial saliva and the flow rate measured.

(iv) Statistical Analysis

A statistical evaluation of the hydraulic conductance data was performed using one-way ANOVA and Tukey means comparison. Data sets were first tested for normal distribution using Shapiro-Wilks normality test.

Figure 2:
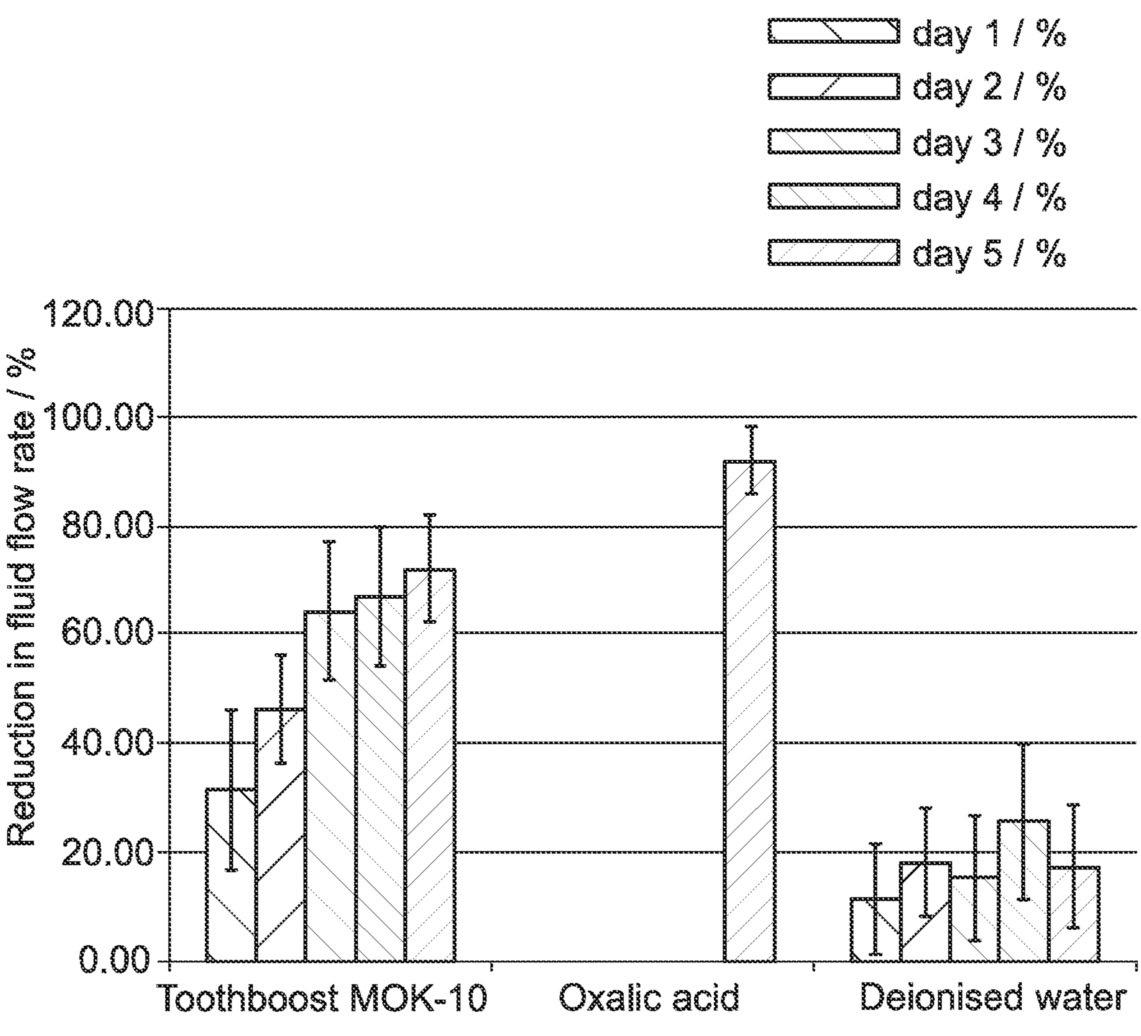
FIG. 2: Measurement of the reduction in flow rate through human dentine when treated with one of: Toothboost MOK formation, 10% oxalic acid solution or deionised water. N=10 human dentine discs per treatment group.

Results: Toothboost MOK-10 reduced the fluid flow rate from the dentine baseline progressively from 31.45% after day one 72.28% after day five. 10% oxalic acid solution reduced the flow rate after day five by 92.28% and deionised water only reduced the flow rate by 17.36% (see FIG. 2 and Table 2). All data sets were normally distributed. When significance=1, $p<0.05$ (see Table 3 for statistical analysis results)

TABLE 3-continued

Pair wise comparison of the liquid formulations show that when Sig = 1 the means difference is significant at the 0.05 level.

| | MeanDiff | SEM | q Value | Prob | Sig | LCL | UCL |
|---|---|---|---|---|---|---|---|
| MOK-10 Deionised water | −54.92 | 4.73 | 16.43 | <0.05 | 1 | −64.85 | −44.99 |
| Oxalic acid Deionised water | 74.91 | 4.08 | 25.97 | <0.05 | 1 | 66.34 | 83.48 |

Conclusion: A comparison of the fluid flow rate reduction for the three formulations shows that 10% oxalic acid reduced the fluid flow rate statistically the greatest. Deionised water statistically reduced the flow rate the least. Toothboost MOK-10 was statistically better than the negative control and demonstrated a high degree of tubule occlusion over the five days with increasing response with repeated application.

TABLE 2

Reduction in the fluid flow rate expressed as a percentage of the initial dentine flow rate before treatment.

| Formulation | Reduction in flow rate after day 1/% | SD | Reduction in flow rate after day 2/% | SD | Reduction in flow rate after day 3/% | SD | Reduction in flow rate after day 4/% | SD | Reduction in flow rate after day 5/% | SD |
|---|---|---|---|---|---|---|---|---|---|---|
| Toothboost MOK-10 | 31.45 | 14.66 | 46.42 | 13.38 | 64.49 | 12.76 | 67.25 | 12.85 | 72.28 | 9.82 |
| Oxalic acid | N/A | N/A | N/A | N/A | N/A | N/A | N/A | N/A | 92.28 | 6.26 |
| Deionised water | 11.35 | 10.33 | 18.13 | 11.91 | 15.38 | 11.47 | 25.67 | 14.26 | 17.36 | 11.28 |

TABLE 3

Pair wise comparison of the liquid formulations show that when Sig = 1 the means difference is significant at the 0.05 level.

| | MeanDiff | SEM | q Value | Prob | Sig | LCL | UCL |
|---|---|---|---|---|---|---|---|
| Day 1 | | | | | | | |
| MOK-10 Deionised water | −20.1 | 5.67 | 5.01 | <0.05 | 1 | −32.02 | −8.19 |
| Day 2 | | | | | | | |
| MOK-10 Deionised water | −28.29 | 5.66 | 7.07 | <0.05 | 1 | −40.19 | −16.4 |
| Day 3 | | | | | | | |
| MOK-10 Deionised water | −49.11 | 5.43 | 12.8 | <0.05 | 1 | −60.51 | −37.71 |
| Day 4 | | | | | | | |
| MOK-10 Deionised water | −41.59 | 6.07 | 9.69 | <0.05 | 1 | −54.34 | −28.83 |
| Day 5 | | | | | | | |
| MOK-10 Oxalic acid | 19.99 | 3.68 | 7.68 | <0.05 | 1 | 12.26 | 27.73 |

Example 9—Effect of Toothboost on Mineral Density Retention when Combined with Fluoride Toothpaste Introduction The objective of this experiment was to determine the change in enamel mineral density during 3 weeks of pH cycling treated with 1100 ppm fluoride toothpaste with and without Toothboost A (MOK) or B (MOL) formulation rinses.

Method

Polished human enamel specimens were subjected to a pH cycling regimen for 15 days consisting of dentifrice treatments, a period of demineralization, and a period of remineralization. Treatments consisted of 1 minute in a 1:3 dentifrice: water slurry. After cycling, specimens were bisected, mounted in resin blocks, and polished. Microscopic images were then taken and analysed with MatLab to determine mineral density and lesion depth.

1100 ppm fluoride toothpaste plus Toothboost A (MOK) or B (MOL) formulations were treated with paste slurry and rinse then inverted and treated with 40 μl per specimen for 2 mins. Specimens were returned to solutions without rinsing.

In addition to AM and PM treatments, 1100 ppm fluoride toothpaste plus Toothboost A (MOK) or B (MOL) were inverted then treated with 40 μl per specimen for 2 mins 3 hours after AM treatment. Specimens were returned to solutions without rinsing.

Figure 3:
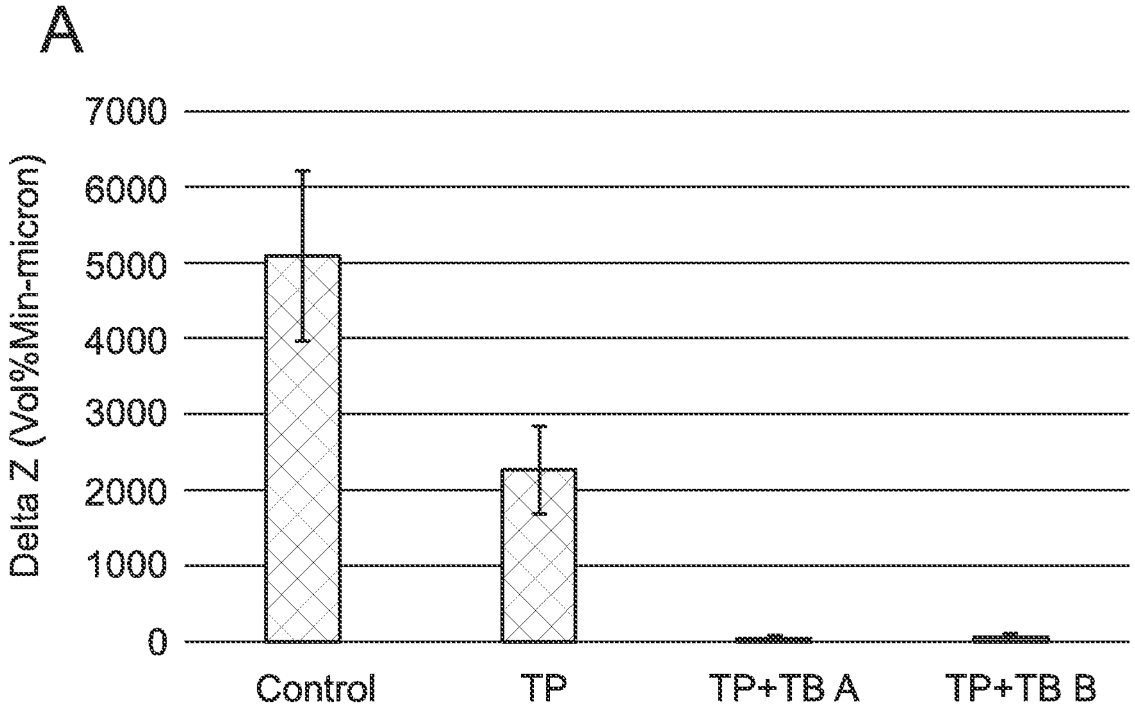
FIG. 3: A; Enamel Mineral Density (DeltaZ—Vol % Min-micron) after 3 Weeks of Cycling±Standard Deviation (SD). B; Lesion Profiles (Mineral Density from Enamel Surface to 350 μm Depth) after 3 Weeks of Cycling.
Figure 3:
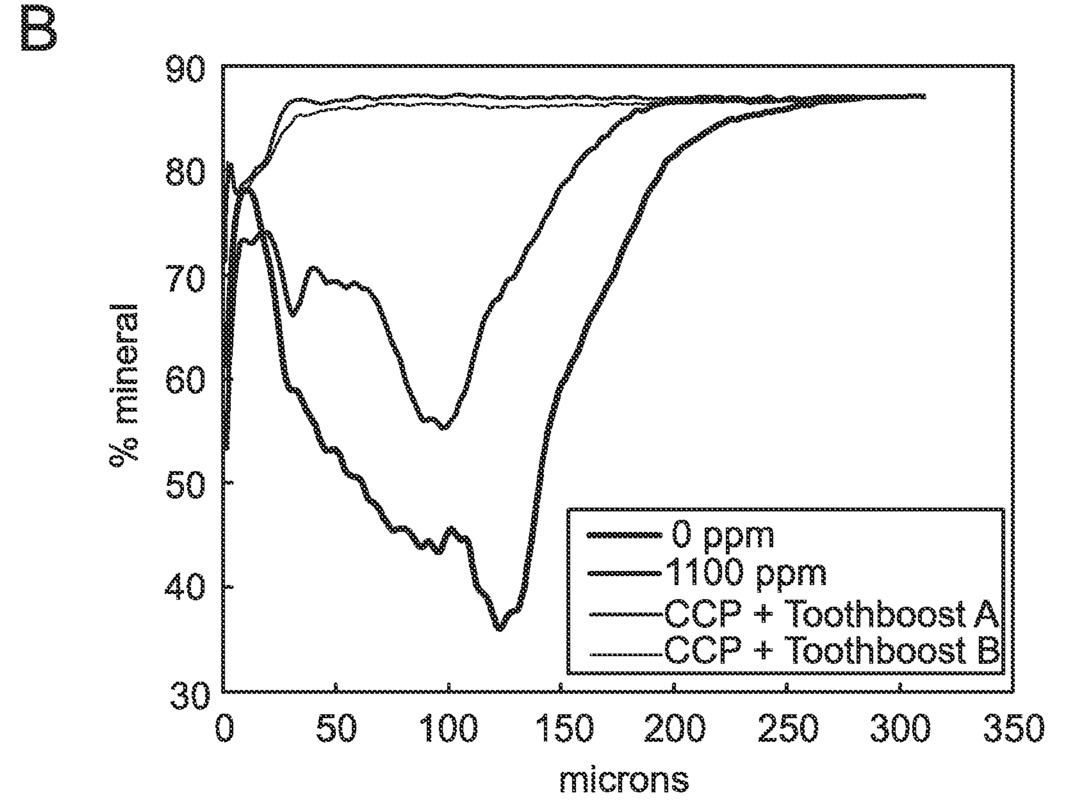

Results 1100 ppm fluoride toothpaste treatment alone or with Toothboost resulted in enamel mineral density that was statistically significantly better than the negative control, 100 ppm low fluoride toothpaste, indicating all have anti-caries efficacy (FIG. 3A). Both Toothboost treatments resulted in a statistically significantly better enamel mineral density than the 1100 ppm fluoride toothpaste treatment alone (FIGS. 3A & B and Table 4).

TABLE 4

Results and Statistical Grouping for Mineral Density (Delta Z), and Lesion Depth (microns)

| Treatment | Code | Mean DeltaZ (Vol % Min-μm) | St. Dev. | Stats Group[1] | Mean Lesion Depth (μm) | St. Dev. |
|---|---|---|---|---|---|---|
| 100 ppm Control Toothpaste | Control | 5090 | 1123 | A | 186 | 30.5 |
| 1100 ppm fluoride toothpaste | TP | 2270 | 574 | B | 143 | 23.3 |
| 1100 ppm fluoride toothpaste + Toothboost A | TP + TB A | 45 | 44 | C | 18 | 6.9 |
| 1100 ppm fluoride toothpaste + Toothboost B | TP + TB B | 59 | 52 | C | 22 | 11.2 |

Conclusion

Toothboost treatment combined with fluoride toothpaste prevents tooth demineralisation and significantly improves enamel mineral density compared to fluoride toothpaste treatment alone. Without wishing to be bound by theory, it is believed that the phosphopeptide contained within the Toothboost formulation stabilises calcium and phosphate ions which itself has remineralising properties and when combined with low levels of fluoride can further enhance the remineralising performance of fluoride alone (Nurrohman, et al., 2022).

Example 10—the Effect of Toothboost Spray and Gel on Dentine Tubule Occlusion

Introduction: A hydraulic conductance study was performed to measure the reduction in fluid flow through human dentine when treated with one of three formulations: Toothboost MOL19 spray, a Toothboost gel MOK11 and deionised water. Human dentine discs were placed into a hydraulic conductance split cell and the fluid flow rate through the untreated dentine tubules measured. The dentine discs in split cells were then treated five time a day for seven days. The fluid flow rates were measured after day 1, 3 and 7 of treatment. The dentine discs were incubated in artificial saliva at 37° C. between treatments and overnight.

Materials and Instruments

Human molars were supplied by Scottish Biomedical and the dentin sections were prepared at Modus Laboratories.

Deionised water from lab supply obtained by reverse osmosis.

EBSS Earles balanced salt solution, Sigma-Aldrich.

Artificial saliva MT2011 (Modus Laboratories Lrd).

Polishing machine: Buehler Automet/Ecomet 250.

P300-a Hydraulic Conductance testing rig.

Methods and procedures are recorded in LNB Modus Labs #0005-81.

Products supplied for this study:

TABLE 5

| The formulations were labelled as indicated above. Formulation |
|---|
| Toothboost MOL19 spray |
| Toothboost gel MOK11 |
| deionised water |

Methods

Specimen Preparation

Sound caries free human molars were sectioned with a wafering saw. A single dentine disc was taken from between the crown and the pulp cavity which was approx. 800 μm thick after sectioning. The discs were then polished flat with P1200 grit paper to a thickness of 500 μm where they were finally polished with P2500 grit paper to give a flat polished dentine surface on both sides of the disc. The discs were then placed into 1% w/w citric acid solution, pH 3.75 and sonicated for five minutes. They were then rinsed with an excess volume of deionised water. Acceptance criteria for the initial flow rate of the discs is between 1.0-20.0 ul/min. N=5 dentine discs were selected for each treatment group. After the baseline hydraulic conductance measurements had been made, the discs were stratified into three groups so that each group had a similar range of initial fluid flow rates.

Hydraulic Conductance Method

The hydraulic conductance equipment was connected to a compressed air supply and the solvent chamber pressurised to 1.0 PSI. A dentine disc was placed into the split cell holding chamber and Earles solution passed through the system. The hydrodynamic flow rate through the dentine was then measured and recorded for five minutes.

Treatment Procedure

The Toothboost spray was applied to the dentine disc, held in the holding chamber, with a single actuation of the pump pack (~0.1 g formulation dispensed). The Toothboost gel was applied by pipetting approximately 0.1 g of the gel directly onto the surface of the dentine. The deionised water was also applied by pipetting approximately 0.1 g of water directly onto the surface of the dentine. The treated dentine was allowed to rest at ambient temperature for two minutes and then the dentine discs within the holding chamber placed into a dedicated container with 20 ml of artificial saliva. The discs were then incubated at 37° C. until the next treatment or overnight.

The treatments were applied approximately at 1 hour intervals throughout the day and remained in the artificial saliva overnight.

Hydraulic Conductance Results

Figure 4:
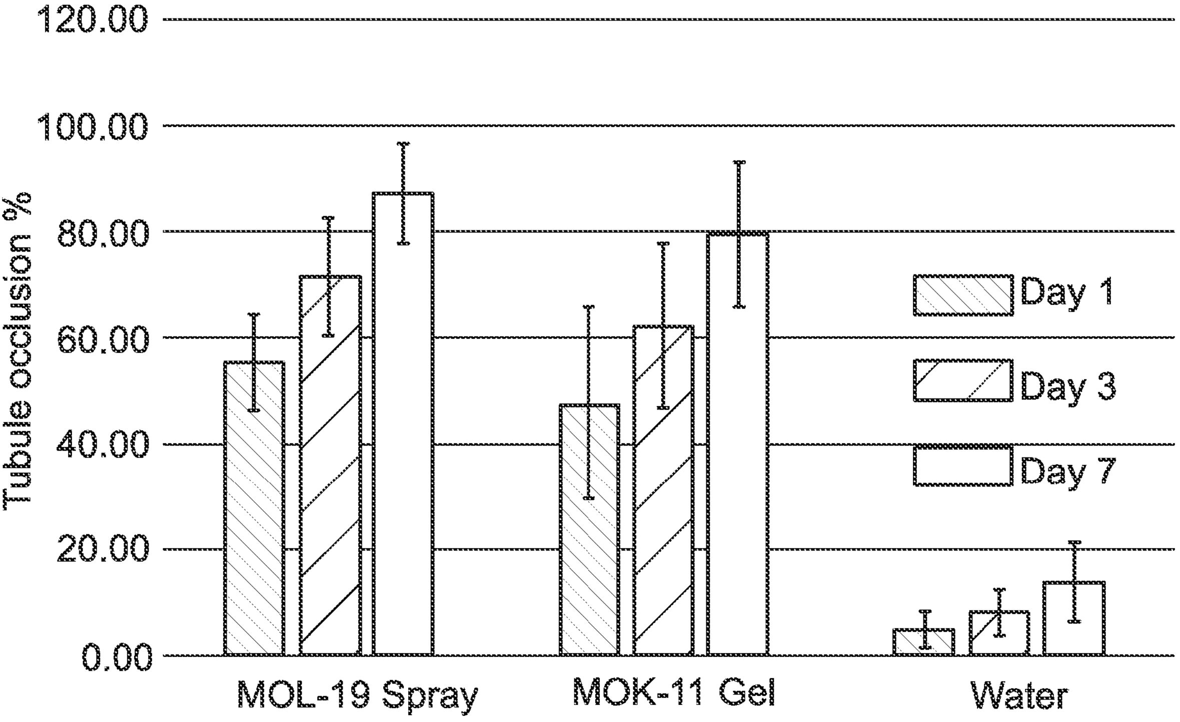
FIG. 4: The reduction in the fluid flow rate expressed as a percentage flow rate reduction. The reduction in fluid flow measured after human dentine discs were treated 5 times a day for 7 days with Toothboost MOL-19 spray, MOK-11 gel or deionised water. N=5 human dentine discs.

Table 6 and FIG. 4 shows the reduction in fluid flow rate from the dentine baseline before treatment compared to the flow rates after treatment, expressed as a percentage reduction.

TABLE 6

The reduction in the fluid flow rate expressed as a percentage of the initial non treated dentine flow rate.

| Formulation | Day 1 | SD | Day 3 | SD | Day 7 | SD |
|---|---|---|---|---|---|---|
| MOL-19 Spray | 55.23 | 9.03 | 71.50 | 11.18 | 87.28 | 9.32 |
| MOK-11 Gel | 47.54 | 18.07 | 62.24 | 15.56 | 79.43 | 13.53 |
| Water | 4.59 | 3.56 | 7.95 | 4.32 | 13.65 | 7.58 |

Statistical Analysis

A statistical evaluation of the hydraulic conductance data was performed using one way ANOVA and Tukey means comparison. Data sets were first tested for normal distribution using Shapiro-Wilks normality test. All data sets had a probability factor greater than 0.05 indicating they were normally distributed.

TABLE 7

Pair wise comparison of the paste formulations show that when Sig = 1 the means difference is significant at the 0.05 level.

| | MeanDiff | SEM | q Value | Prob | Sig | LCL | UCL |
|---|---|---|---|---|---|---|---|
| Day 1 | | | | | | | |
| MOL-19 spray MOK-11 gel | −7.69 | 9.04 | 1.20 | 0.42 | 0 | −28.52 | 13.15 |
| MOL-19 spray Neg control | −50.64 | 4.34 | 16.49 | <0.05 | 1 | −60.65 | −40.62 |
| MOK-gel Neg control | 42.95 | 8.24 | 7.37 | <0.05 | 1 | 23.95 | 61.95 |
| Day 3 | | | | | | | |
| MOL-19 spray MOK-11 gel | −9.25 | 8.57 | 1.53 | 0.31 | 0 | −29.01 | 10.50 |
| MOL-19 spray Neg control | −63.54 | 5.36 | 16.76 | <0.05 | 1 | −75.90 | −51.18 |
| MOK-gel Neg control | 54.29 | 7.22 | 10.63 | <0.05 | 1 | 37.64 | 70.94 |
| Day 7 | | | | | | | |
| MOL-19 spray MOK-11 gel | −7.86 | 7.35 | 1.51 | 0.32 | 0 | −24.80 | 9.09 |
| MOL-19 spray Neg control | −73.64 | 5.38 | 19.37 | <0.05 | 1 | −86.03 | −61.24 |
| MOK-gel Neg control | 65.78 | 6.94 | 13.41 | <0.05 | 1 | 49.78 | 81.78 |

Conclusion

A comparison of the fluid flow rate reduction for the three formulations shows that after days 1, 3 and 7 MOL-19 spray was statistically the same as MOK-11 gel. The spray and gel were statistically greater than deionised water at all time points. The tubule occluding ability of the spray and gel formulations is considered to be good, reaching about 80% after day seven. A common feature of Toothboost products is that regular and frequent application enhances the activity of the treatment, in this case, tubule occlusion.

REFERENCES

Nurrohman, H. et al., 2022. The Role of Process-Directing Agents on Enamel Lesion Remineralization: Fluoride Boosters. *Biomimetics,* 7(54).

The invention claimed is:

1. A method of treatment to reduce dental hypersensitivity in a subject in need thereof, wherein the method comprises administering to the subject's oral cavity a therapeutically effective amount of a composition comprising a phosphopeptide, and wherein further the composition does not comprise additional phosphate or an additional source of phosphate.

2. The method according to claim 1, wherein the phosphopeptide comprises osteopontin or phosphopeptides derived therefrom, and/or casein or phosphopeptides derived therefrom, and/or wherein the composition comprises less than 50 mM phosphate.

3. The method according to claim 1, wherein:

the composition further comprises fluoride or a source of fluoride; or the composition does not comprise fluoride or a source of fluoride; or the composition further comprises calcium or a source of calcium.

4. The method according to claim 1, wherein the composition comprises from about 20% to about 90% by weight water.

5. The method according to claim 1, wherein:

the composition is a liquid and wherein the composition comprises at least 50% by weight water; or the composition is a colloid and wherein the composition comprises less than or equal to 25% by weight water.

6. The method according to claim 1, wherein the composition comprises one or more further components selected from: alcohol(s), humectant(s), surfactant(s), preservative(s), flavouring agent(s), sweetening agent(s), colouring agent(s), anti-caries agent(s), buffer(s), acid(s), base(s), whitening agent(s), thickener(s), and anticalculus agent(s).

7. The method according to claim 1, wherein the composition comprises:

a phosphopeptide from about 0.5% to about 15% by weight;

water from about 20% to about 99% by weight;

a buffer from about 1% to about 20% by weight;

a flavouring, preservative and/or other ingredients from 0% to about 70% by weight;

a sweetener from about 0.1% to about 20% by weight;

optionally a source of calcium ions from about 0.1% to about 15% by weight;

optionally a source of phosphate ions from about 0.2% to about 32% by weight;

optionally a source of fluoride from about 0.01% to about 3% by weight; and optionally a thickener from about 0.1% to about 20% by weight;

or wherein the composition comprises:

a phosphopeptide in an amount of about 3% w/w;

a buffer in an amount of about 15% w/w;

water in an amount of about 54 to 66% w/w;

a source of calcium in an amount of about 3% w/w;

a flavouring and preservative agent in an amount of about 8% w/w;

optionally a source of fluoride in an amount of about 0.4% w/w;

a sweetener in an amount of about 5% w/w; and optionally an acid in an amount of about 11% w/w;

or wherein the composition comprises:

a phosphopeptide in an amount of about 3% w/w;

a buffer in an amount of about 2% w/w;

a whitening agent in an amount of about 6% w/w;

water in an amount of about 23 to 25% w/w;

an acid in an amount of about 34% w/w;

a source of calcium in an amount of about 0.5% w/w;

a sweetener in an amount of about 9% w/w;

a thickener in an amount of about 13% w/w; and a flavouring and preservative agent in an amount of about 8% w/w;

or wherein the composition comprises:

a phosphopeptide in an amount of about 3% w/w;

a buffer in an amount of about 15% w/w;

water in an amount of about 30% w/w;

a source of calcium in an amount of about 3% w/w;

a source of phosphate;

a sweetener in an amount of about 5% w/w;

a flavouring and preservative agent in an amount of about 8% w/w; and optionally, a source of fluoride.

8. The method according to claim 1, wherein the composition is administered to the subject's oral cavity at least once per day, and optionally the composition is administered to the subject's oral cavity prior to sleep, after eating, and/or after drinking.

9. The method according to claim 1, wherein:

the composition does not comprise a phosphate buffer.

10. A method of treatment of xerostomia in a subject in need thereof, wherein the method comprises administering to the subject's oral cavity a therapeutically effective amount of a composition comprising a phosphopeptide, and wherein further the composition does not comprise additional phosphate or an additional source of phosphate.

11. The method according to claim 10, wherein:

the composition does not comprise a phosphate buffer.

12. The method according to claim 10, wherein:

the phosphopeptide comprises osteopontin or phosphopeptides derived therefrom, and/or casein or phosphopeptides derived therefrom; and/or the composition comprises less than 50 mM phosphate.

13. The method according claim 10, wherein:

the composition further comprises fluoride or a source of fluoride; or the composition does not comprise fluoride or a source of fluoride; or the composition further comprises calcium or a source of calcium.

14. The method according claim 10, wherein:

the composition comprises between about 20 to about 90% by weight water; or the composition is a liquid and wherein the composition comprises at least 50% by weight water; or the composition is a colloid and wherein the composition comprises less than or equal to 25% by weight water.

15. The method according claim 10, wherein the composition comprises one or more further components selected from: alcohol(s), humectant(s), surfactant(s), preservative(s), flavouring agent(s), sweetening agent(s), colouring agent(s), anti-caries agent(s), buffer(s), acid(s), base(s), whitening agent(s), thickener(s), and anticalculus agent(s).

16. The method according claim 10, wherein the composition comprises:

a phosphopeptide from about 0.5% to about 15% by weight;

water from about 20% to about 99% by weight;

a buffer from about 1% to about 20% by weight;

a flavouring, preservative and/or other ingredients from 0% to about 70% by weight;

a sweetener from about 0.1% to about 20% by weight;

optionally a source of calcium ions from about 0.1% to about 15% by weight;

optionally a source of phosphate ions from about 0.2% to about 32% by weight;

optionally a source of fluoride from about 0.01% to about 3% by weight; and optionally a thickener from about 0.1% to about 20% by weight;

or wherein the composition comprises:

a phosphopeptide in an amount of about 3% w/w;

a buffer in an amount of about 15% w/w;

water in an amount of about 54 to 66% w/w;

a source of calcium in an amount of about 3% w/w;

a flavouring and preservative agent in an amount of about 8% w/w, optionally a source of fluoride in an amount of about 0.4% w/w;

a sweetener in an amount of about 5% w/w; and optionally an acid in an amount of about 11% w/w;

or wherein the composition comprises:

a phosphopeptide in an amount of about 3% w/w;

a buffer in an amount of about 2% w/w;

a whitening agent in an amount of about 6% w/w;

water in an amount of about 23 to 25% w/w;

an acid in an amount of about 34% w/w;

a source of calcium in an amount of about 0.5% w/w;

a sweetener in an amount of about 9% w/w;

a thickener in an amount of about 13% w/w;

a flavouring and preservative agent in an amount of about 8% w/w; and optionally a source of fluoride in an amount of about 1% w/w;

or wherein the composition comprises:

a phosphopeptide in an amount of about 3% w/w;

a buffer in an amount of about 15% w/w;

water in an amount of about 30% w/w;

a source of calcium in an amount of about 3% w/w;

a source of phosphate, a sweetener in an amount of about 5% w/w;

a flavouring and preservative agent in an amount of about 8% w/w, and optionally, a source of fluoride.

17. The method according to claim 10, wherein the composition is administered to the subject's oral cavity at least once per day, and optionally the composition is administered to the subject's oral cavity prior to sleep, after eating, and/or after drinking.

18. A method of treatment of demineralisation of an oral surface, dental caries and/or candidiasis infection in a subject having xerostomia, wherein the method comprises administering to the subject's oral cavity a therapeutically effective amount of a composition comprising a phosphopeptide, and wherein further the composition does not comprise additional phosphate or an additional source of phosphate.

19. A method of maintaining enamel mineral density in a subject having hypersensitivity and/or xerostomia, wherein the method comprises administering to the subject's oral cavity a therapeutically effective amount of a composition comprising a phosphopeptide, and wherein further the composition does not comprise additional phosphate or an additional source of phosphate.

20. The method according to claim 19, wherein:

the composition does not comprise a phosphate buffer.

21. The method according to claim 19, wherein:

the phosphopeptide comprises osteopontin or phosphopeptides derived therefrom, and/or casein or phosphopeptides derived therefrom; and/or the composition comprises less than 50 mM phosphate.

* * * * *